US012685818B2

(12) United States Patent
Ellerbusch et al.

(10) Patent No.: US 12,685,818 B2
(45) Date of Patent: Jul. 21, 2026

(54) FLOW SENSOR SYSTEM

(71) Applicant: Becton, Dickinson and Company, Franklin Lakes, NJ (US)

(72) Inventors: Gary Ellerbusch, Nutley, NJ (US); Hong Zhu, Glen Rock, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 120 days.

(21) Appl. No.: 18/434,161

(22) Filed: Feb. 6, 2024

(65) Prior Publication Data

US 2024/0173476 A1      May 30, 2024

Related U.S. Application Data

(63) Continuation of application No. 17/159,320, filed on Jan. 27, 2021, now Pat. No. 11,925,787.

(Continued)

(51) Int. Cl.
*A61M 5/168* (2006.01)
*A61M 5/145* (2006.01)
(Continued)

(52) U.S. Cl.
CPC ...... *A61M 5/16831* (2013.01); *A61M 5/1452* (2013.01); *G01F 1/667* (2013.01); *H04B 1/06* (2013.01); *H04W 4/80* (2018.02); *A61M 2205/3334* (2013.01); *A61M 2205/3561* (2013.01); *A61M 2205/502* (2013.01)

(58) Field of Classification Search
CPC ............ A61M 5/16831; A61M 5/1452; A61M 2205/3334; A61M 2205/3561; A61M 2205/502; A61M 5/1413; A61M 5/16886; A61M 2039/0205; A61M 2039/229; A61M 2205/3569; A61M 2205/505; A61M 2205/6009; A61M 2205/6054; A61M 2205/6063; A61M 2209/084; A61M 5/16881; G01F 1/667; G01F 15/005; G01F 15/063; H04B 1/06; H04W 4/80

See application file for complete search history.

(56) References Cited

U.S. PATENT DOCUMENTS 10,391,241 B2     8/2019   Desch et al.
11,925,787 B2 *   3/2024   Ellerbusch .......... A61M 5/1452
(Continued)

FOREIGN PATENT DOCUMENTS

WO          2015149191 A1    10/2015
WO      WO2017021226 A1     2/2017
WO          2017038575 A1    3/2017

OTHER PUBLICATIONS

WO2017038575A1 Machine Translation of Written Description (Year: 2017).*

*Primary Examiner* — James D Ponton
(74) *Attorney, Agent, or Firm* — The Webb Law Firm

(57) ABSTRACT

A system may include a flow sensor and a base. The flow sensor may be configured to connect to the base. The flow sensor may include a flow tube including a fluid inlet at a first end of the flow tube, a fluid outlet at a second end of the flow tube opposite the first end of the flow tube, and a fluid injection port between the first end and the second end of the flow tube. The base may include a short range wireless communication device including a curved coil antenna.

22 Claims, 24 Drawing Sheets

Related U.S. Application Data

(60) Provisional application No. 62/966,281, filed on Jan. 27, 2020.

(51) Int. Cl.
G01F 1/667 (2022.01)
H04B 1/06 (2006.01)
H04W 4/80 (2018.01)

(56) References Cited

U.S. PATENT DOCUMENTS

| | | | |
|---|---|---|---|
| 2003/0233069 A1* | 12/2003 | Gillespie, Jr. ............ | G01B 7/00 604/131 |
| 2013/0184676 A1* | 7/2013 | Kamen ............... | A61M 5/1458 604/152 |
| 2013/0204227 A1* | 8/2013 | Bochenko .............. | G16H 10/60 604/189 |
| 2015/0273144 A1 | 10/2015 | Lee | |
| 2017/0059376 A1 | 3/2017 | Bochenko | |
| 2017/0319787 A1 | 11/2017 | Roedle | |
| 2019/0297682 A1 | 9/2019 | Liebert et al. | |

* cited by examiner

PATIENT WRISTBAND

180

180

POWER ON READER & ASSIGN PATIENT

196

106

180

160

160

180

106

ASSEMBLE READER TO SENSOR & READY FOR MED ADMINISTRATION

104 fentaNYL 50 mcg/mL

Simulated Medication Prep: 2/7/2020 1:59
(Not For Human Use) Exp: 2/7/2020 23:59

BATCH
LOT CODE

By:
GWXXYZ

102

104 fentaNYL

GENERATE LABELS BY "SCAN & PRINT" & BARREL LABEL SYRINGES

106

160

104

102

180

180

102

106

106

CONNECT LABELED SYRINGES, IDENTIFY

150

163

162

102

166

180

160

164 h-field(f=13.56)[1]
FREQUENCY    13.56 MHz
PHASE    0°
CROSS SECTION    A
CUTPLANE AT X    0.000 mm
MAXIMUM (PLANE)    176.016 A/m
MAXIMUM    1062.14 A/m NOTES:
1. SENSOR & PATIENT ASSOCIATION MAY BE INTERCHANGEABLE IN ORDER
2. PATIENT TRANSFER REFERS TO POINTS WHERE THE INJECTION SITE REQUIRES DISSASSEMBLY AFTER ASSOCIATION

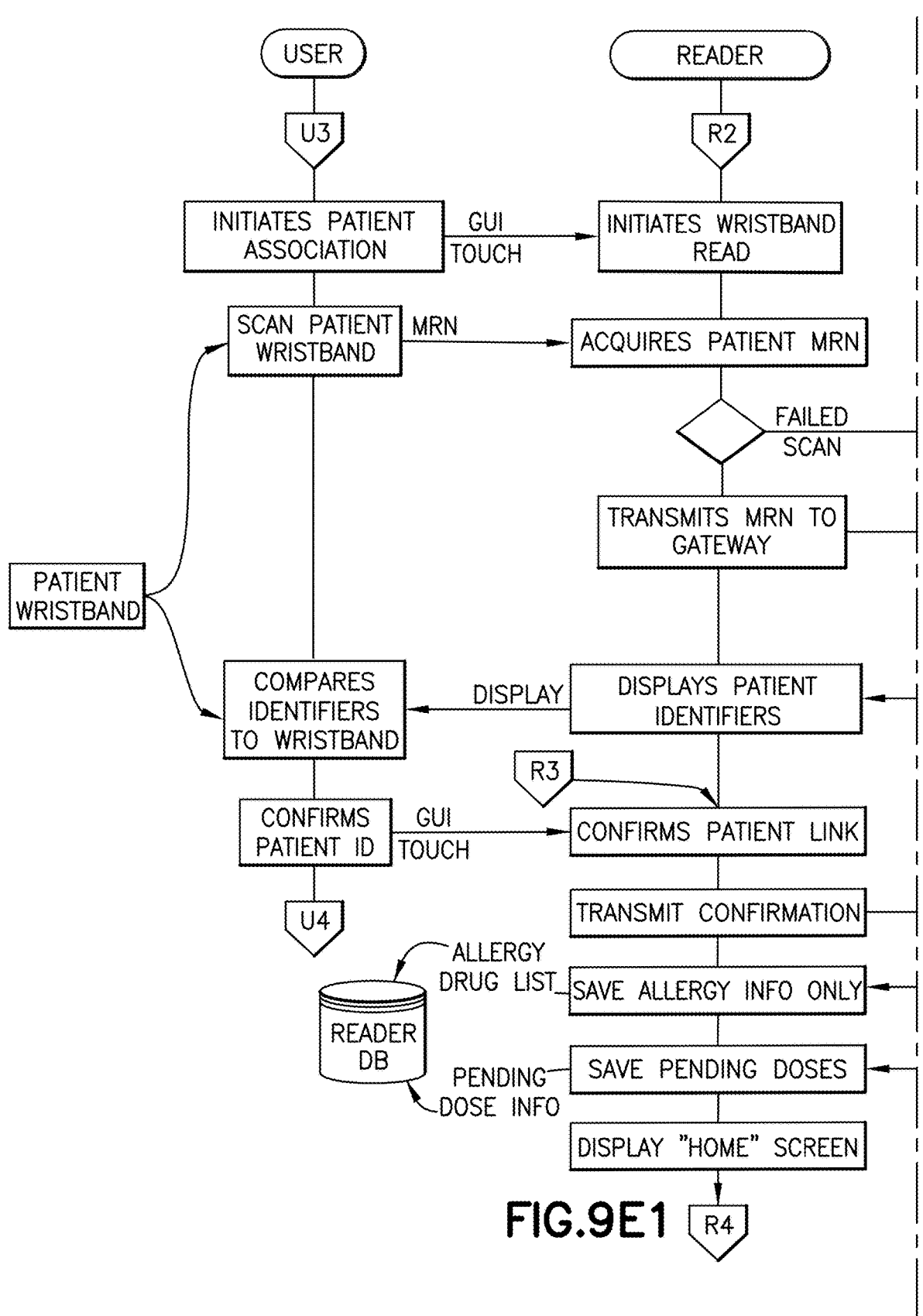
FIG.9E1

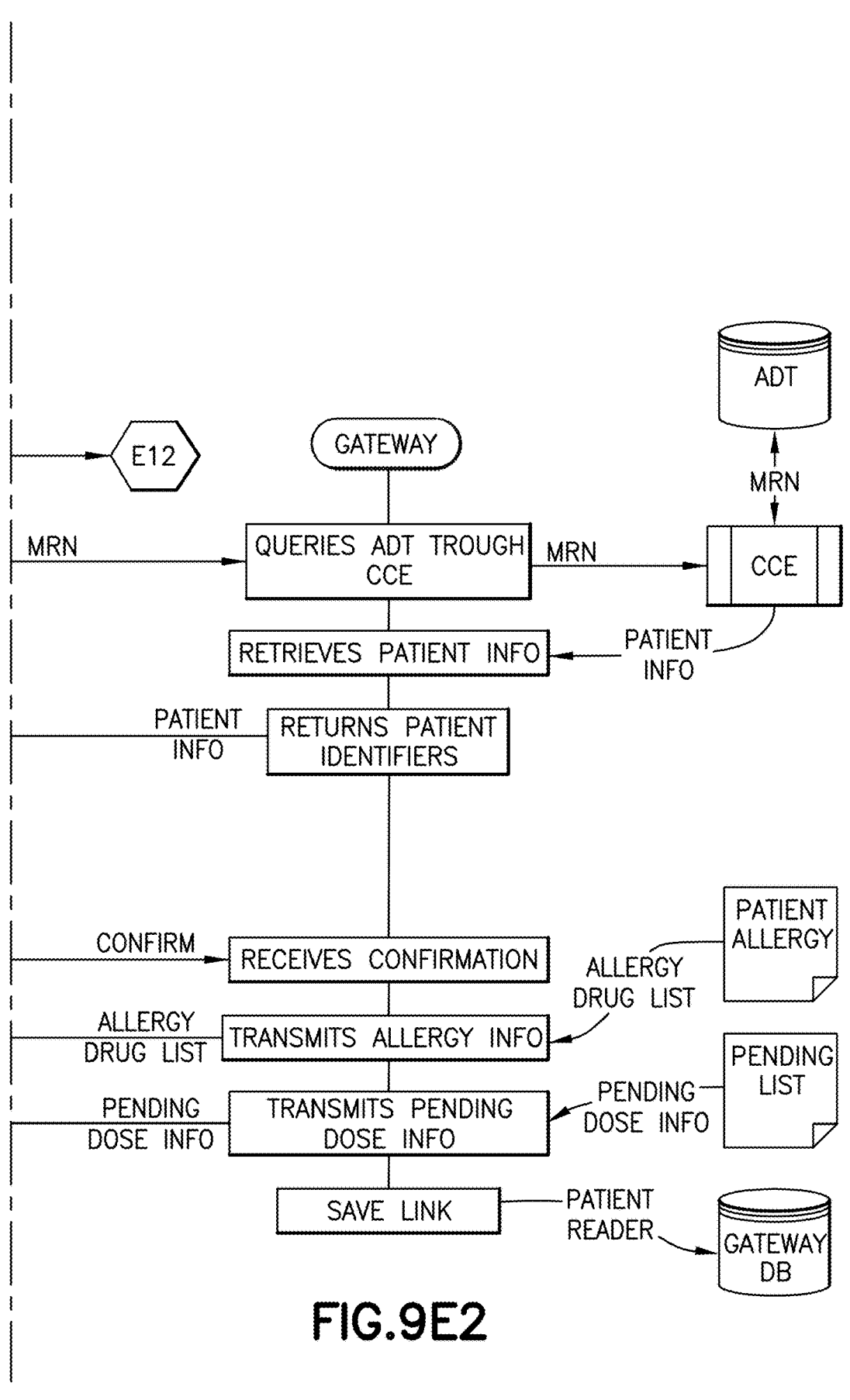
FIG.9E2

FLOW SENSOR SYSTEM

CROSS-REFERENCE TO RELATED APPLICATION

The present application is a continuation of U.S. patent application Ser. No. 17/159,320, entitled "Flow Sensor System", filed Jan. 27, 2021, which claims priority to U.S. Provisional Application Ser. No. 62/966,281, entitled "Flow Sensor System", filed Jan. 27, 2020, the entire disclosures of each of which are hereby incorporated by reference in its entirety.

BACKGROUND

1. Field

The present disclosure relates generally to a flow sensor system and, in some non-limiting embodiments or aspects, to a flow sensor system for sensing a flow of a fluidic medicament.

2. Technical Considerations

There is a need to reduce medication error at bedside during bolus delivery. It is advantageous to provide a record of, and electronically measure, bolus delivery which allows monitoring bolus delivery and automatic documentation of bolus delivery as part of a patient's health record. Additionally, it is advantageous to provide alerts when bolus delivery inconsistent with a patient's medical record is about to occur.

SUMMARY

Non-limiting embodiments or aspects are set forth in the following numbered clauses:

Clause 1. A system including: a flow sensor including: a flow tube including a fluid inlet at a first end of the flow tube, a fluid outlet at a second end of the flow tube opposite the first end of the flow tube, a fluid injection port between the first end and the second end of the flow tube, and a valve configured to control a flow of a fluid in the flow tube; at least one sensor configured to characterize at least one attribute of the fluid in the flow tube; and a flow sensor electrical contact in electrical communication with the at least one sensor; and a base configured to connect to the flow sensor, wherein the base includes: one or more processors; a base electrical contact in electrical communication with the one or more processors; a short range wireless communication device; and a display, wherein the flow sensor electrical contact is in electrical communication with the base electrical contact when the flow sensor is connected to the base.

Clause 2. The system of clause 1, wherein the valve is configured transition between a plurality of different states to control at least one of: the flow of the fluid between the fluid inlet and the fluid outlet, the flow of the fluid between the fluid inlet and the fluid injection port, the flow of the fluid between the fluid injection port and the fluid outlet, or any combination thereof.

Clause 3. The system of any of clauses 1 and 2, wherein the one or more processors are programmed and/or configured to automatically detect a state of the valve when the flow sensor is connected to the base.

Clause 4. The system of any of clauses 1-3, wherein the one or more processors are programmed and/or configured to determine whether to record information associated with the at least one attribute of the fluid in the flow tube based on the detected state of the valve.

Clause 5. The system of any of clauses 1-4, wherein the one or more processors are programmed and/or configured to automatically detect a connection of the flow sensor to the base.

Clause 6. The system of any of clauses 1-5, wherein the one or more processors are programmed and/or configured to automatically detect a connection of a syringe to the fluid injection port of the flow sensor.

Clause 7. The system of any of clauses 1-6, wherein the display includes a touchscreen display configured to receive user input from a user.

Clause 8. The system of any of clauses 1-7, wherein the flow sensor is inserted in-line with an IV line between a fluid source and a patient.

Clause 9. The system of any of clauses 1-8, wherein the short range wireless communication device is configured to automatically communicate with a short range wireless communication tag on a syringe via a short range wireless communication connection when the short range wireless communication tag is brought within a communication range of the short range wireless communication device.

Clause 10. The system of any of clauses 1-9, wherein the short range wireless communication device includes a near-field communication (NFC) receiver.

Clause 11. The system of any of clauses 1-10, wherein the base further includes a wireless communication device configured to communicate information associated with the at least one attribute of the fluid in the flow tube to a remote computing device.

Clause 12. The system of any of clauses 1-11, wherein the base further includes an optical scanner configured to read a bar code label.

Clause 13. The system of any of clauses 1-12, wherein the base further includes an opening configured to receive the flow sensor, and wherein the flow sensor is configured for sliding engagement with the opening of the base.

Clause 14. A flow sensor, including: a flow tube including a fluid inlet at a first end of the flow tube, a fluid outlet at a second end of the flow tube opposite the first end of the flow tube, a fluid injection port between the first end and the second end of the flow tube, and a valve configured to control a flow of a fluid in the flow tube; at least one sensor configured to characterize at least one attribute of the fluid in the flow tube; a flow sensor electrical contact in electrical communication with the at least one sensor.

Clause 15. The flow sensor of clause 14, wherein the valve is configured transition between a plurality of different states to control at least one of: the flow of the fluid between the fluid inlet and the fluid outlet, the flow of the fluid between the fluid inlet and the fluid injection port, the flow of the fluid between the fluid injection port and the fluid outlet, or any combination thereof.

Clause 16. The flow sensor of any of clauses 14 and 15, wherein the flow sensor is inserted in-line with an IV line between a fluid source and a patient.

Clause 17. A base for a flow sensor, including: one or more processors; a base electrical contact in electrical communication with the one or more processors; a short range wireless communication device; and a display, wherein the base sensor electrical contact is in electrical communication with at least one sensor of the flow sensor when the flow sensor is connected to the base.

Clause 18. The base of clause 17, wherein the one or more processors are programmed and/or configured to automatically detect a state of a valve of the flow sensor when the flow sensor is connected to the base.

Clause 19. The base of any of clauses 17 and 18, wherein the one or more processors are programmed and/or configured to determine whether to record information associated with at least one attribute of a fluid sensed by the flow sensor based on the detected state of the valve.

Clause 20. The base of any of clause 17-19, wherein the one or more processors are programmed and/or configured to automatically detect a connection of the flow sensor to the base.

Clause 21. The base of any of clauses 17-20, wherein the one or more processors are programmed and/or configured to automatically detect a connection of a syringe to the flow sensor.

Clause 22. The base of any of clauses 17-21, wherein the display includes a touchscreen display configured to receive user input from a user.

Clause 23. The base of any of clauses 17-22, wherein the short range wireless communication device is configured to automatically communicate with a short range wireless communication tag on a syringe via a short range wireless communication connection when the short range wireless communication tag is brought within a communication range of the short range wireless communication device.

Clause 24. The base of any of clauses 17-23, wherein the short range wireless communication device includes a near-field communication (NFC) receiver.

Clause 25. The base of any of clauses 17-24, wherein the base further includes a wireless communication device configured to communicate information associated with the at least one attribute of the fluid in the flow tube to a remote computing device.

Clause 26. The base of any of clauses 17-25, wherein the base further includes an optical scanner configured to read a bar code label.

Clause 27. The base of any of clauses 17-26, wherein the base further includes an opening configured to receive the flow sensor, and wherein the flow sensor is configured for sliding engagement with the opening of the base.

Clause 28. A system including: a flow sensor including: a flow tube including a fluid inlet at a first end of the flow tube, a fluid outlet at a second end of the flow tube opposite the first end of the flow tube, a fluid injection port between the first end and the second end of the flow tube, wherein the fluid injection port extends from the flow tube in a first direction parallel to a longitudinal axis of the fluid injection port; and a base configured to connect to the flow sensor, wherein the base includes: a short range wireless communication device including a curved coil antenna, wherein the curved coil antenna is radially curved with respect to the longitudinal axis of the fluid injection port when the flow sensor is connected to the base.

Clause 29. The system of clause 28, wherein the curved coil antenna extends in the first direction parallel to the longitudinal axis of the fluid injection port.

Clause 30. The system of any of clauses 28-30, wherein the base further includes a display, and wherein the curved coil antenna extends in a direction parallel to a plane defined by a face of the display.

Clause 31. The system of any of clauses 28-30, wherein the base further includes a display, and wherein the curved coil antenna extends in a direction perpendicular to a plane defined by a face of the display.

Clause 32. The system of any of clauses 28-31, wherein the fluid injection port is configured to connect to a syringe, and wherein, when the syringe is connected to the fluid injection port of the flow sensor and the flow sensor is connected to the base, the curved coil antenna is radially curved around the syringe.

Clause 33. The system of any of clauses 28-32, wherein a short range wireless communication tag attached is attached to a body of the syringe.

Clause 34. The system of any of clauses 28-33, wherein the short range wireless communication device is configured to automatically communicate with the short range wireless communication tag on the syringe via a short range wireless communication connection when the short range wireless communication tag is brought within a communication range of the short range wireless communication device.

Clause 35. The system of any of clauses 28-34, wherein the short range wireless communication device receives information associated with a medication included in the syringe from the short range wireless communication tag when the short range wireless communication tag is brought within the communication range of the short range wireless communication device.

Clause 36. The system of any of clauses 28-35, wherein the short range wireless communication device includes a near-field communication (NFC) receiver.

Clause 37. A system including: a flow sensor including: a flow tube including a fluid inlet at a first end of the flow tube, a fluid outlet at a second end of the flow tube opposite the first end of the flow tube, a fluid injection port between the first end and the second end of the flow tube, wherein the fluid injection port is configured to connect to a syringe; and a base configured to connect to the flow sensor, wherein the base includes: a short range wireless communication device including a curved coil antenna, wherein, when the syringe is connected to the fluid injection port of the flow sensor and the flow sensor is connected to the base, the curved coil antenna is radially curved around the syringe.

Clause 38. The system of clause 37, wherein the curved coil antenna extends in a first direction parallel to a longitudinal axis of the syringe when the syringe is connected to the fluid injection port of the flow sensor and the flow sensor is connected to the base.

Clause 39. The system of any of clauses 37 and 38, wherein the base further includes a display, and wherein the curved coil antenna extends in a direction parallel to a plane defined by a face of the display.

Clause 40. The system of any of clauses 37-39, wherein the base further includes a display, and wherein the curved coil antenna extends in a direction perpendicular to a plane defined by a face of the display.

Clause 41. The system of any of clauses 27-40, wherein a short range wireless communication tag attached is attached to a body of the syringe.

Clause 42. The system of any of clauses 27-41, wherein the short range wireless communication device is configured to automatically communicate with the short range wireless communication tag on the syringe via a short range wireless communication connection when the short range wireless communication tag is brought within a communication range of the short range wireless communication device.

Clause 43. The system of any of clauses 27-42, wherein the short range wireless communication device receives information associated with a medication included in the syringe from the short range wireless communication tag when the short range wireless communication tag is brought within the communication range of the short range wireless communication device.

Clause 44. The system of any of clauses 27-43, wherein the short range wireless communication device includes a near-field communication (NFC) receiver.

Clause 45. A base for a flow sensor, including: a housing including: an opening configured to receive the flow sensor; one or more processors; a display; and a short range wireless communication device including a curved coil antenna.

Clause 46. The base of clause 45, wherein the curved coil antenna extends in a direction parallel to a plane defined by a face of the display.

Clause 47. The base of any of clauses 45 and 46, wherein the curved coil antenna extends in a direction perpendicular to a plane defined by a face of the display.

Clause 48. The system of any of clauses 45-47, wherein the curved coil antenna is radially curved around a syringe when the syringe is connected to the flow sensor and the flow sensor is connected to the base.

Clause 49. The system of any of clauses 45-48, wherein a short range wireless communication tag attached is attached to a body of the syringe.

Clause 50. The system of any of clauses 45-49, wherein the short range wireless communication device is configured to automatically communicate with the short range wireless communication tag on the syringe via a short range wireless communication connection when the short range wireless communication tag is brought within a communication range of the short range wireless communication device.

Clause 51. The system of any of clauses 45-50, wherein the short range wireless communication device receives information associated with a medication included in the syringe from the short range wireless communication tag when the short range wireless communication tag is brought within the communication range of the short range wireless communication device.

Clause 52. The system of any of clauses 45-51, wherein the short range wireless communication device includes a near-field communication (NFC) receiver.

Clause 53. A method including: scanning, with an optical scanner of a base for a disposable flow sensor, a flow sensor label attached to the disposable flow sensor to decode a flow sensor identifier associated with the flow sensor; scanning, with the optical scanner of the base for the disposable flow sensor, a patient label attached to a patient to decode a patient identifier associated with the patient; connecting the disposable flow sensor to the base.

Clause 54. The method of clause 53, further including: integrating the disposable flow sensor into an IV line.

Clause 55. The method of any of clauses 53 and 54, wherein the disposable flow sensor is integrated into the IV line before scanning the flow sensor label, scanning the patient label, and connecting the disposable flow sensor to the base.

Clause 56. The method of any of clauses 53-55, wherein the disposable flow sensor is integrated into the IV line after scanning the flow sensor label, scanning the patient label, and connecting the disposable flow sensor to the base.

Clause 57. The method of any of clauses 53-56, further including: communicating, with the base, the flow sensor identifier and the patient identifier to a remote computing device; associating, with the remote computing device in a database, the flow sensor identifier with the patient identifier.

Clause 58. The method of any of clauses 53-57, further including: communicating, with the base, to a remote computing device, a request for a status of the flow sensor associated with the flow sensor identifier; receiving, with the base, from the remote computing device, an indication of the status of the flow sensor associated with the flow sensor identifier, wherein the indication of the status of the flow sensor includes an indication of whether the flow sensor identifier of the flow sensor is associated with the patient identifier of the patient.

Clause 59. The method of any of clauses 53-58, further including: communicating, with the base, to the remote computing device, a base identifier associated with the base in the request for the status of the flow sensor associated with the flow sensor identifier; and associating, with the remote computing device in a database, the base identifier with the flow sensor identifier and the patient identifier.

Clause 60. The method of any of clauses 53-59, further including: communicating, with the base, to the remote computing device, a request for information associated with the patient associated with the patient identifier; receiving, with the base, from the remote computing device, the information associated with the patient; and displaying, with a display of the base, the information associated with the patient.

Clause 61. The method of any of clauses 53-60, wherein the information associated with the patient includes at least one of a list of medication allergies associated with the patient and a list of medication doses pending for the patient.

Clause 62. The method of any of clauses 53-61, further including: scanning, with a short range wireless communication device of the base, a short range wireless communication tag attached to a syringe to decode a medication identifier associated with a medication in the syringe; comparing, with the base, the medication identifier to the at least one of the list of medication allergies associated with the patient and the list of medication doses pending for the patient; and displaying, with the display of the base, an alert associated with administration of the medication to the patient.

Clause 63. The method of any of clauses 53-62, wherein the short range wireless communication device includes a near-field communication (NFC) receiver, and wherein the short range wireless communication tag includes a NFC tag.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which:

FIG. 9E1 is a flowchart of non-limiting embodiments or aspects of a process for using a flow sensor system; and FIG. 9E2 is a flowchart of non-limiting embodiments or aspects of a process for using a flow sensor system.

DETAILED DESCRIPTION

Figure 1:
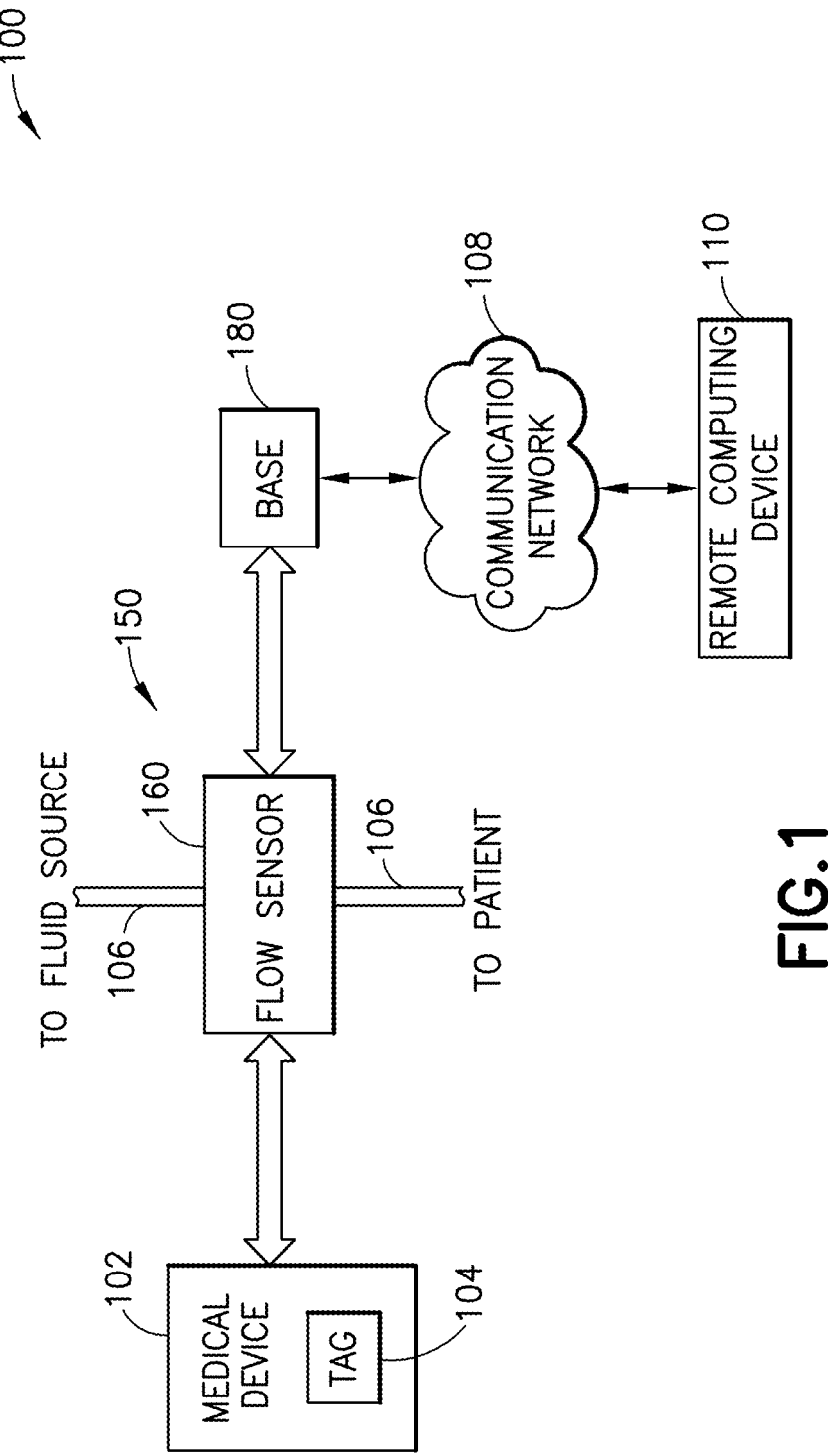
FIG. 1 is a diagram of non-limiting embodiments or aspects of an environment in which systems, devices, products, apparatus, and/or methods, described herein, may be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments disclosed herein are not to be considered as limiting unless otherwise indicated.

As used herein, proximal shall refer to a part or direction located away or furthest from a patient (upstream), while distal shall refer to a part or direction towards or located nearest to a patient (downstream). Also, a drug substance is used herein in an illustrative, non-limiting manner to refer to any substance injectable into the body of a patient for any purpose. Reference to a patient may be to any being, human or animal. Reference to a clinician may be to any person or thing giving treatment, e.g., a nurse, doctor, machine intelligence, caregiver, or even self-treatment.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one."

Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least in partially on" unless explicitly stated otherwise.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, the term "computing device" or "computer device" may refer to one or more electronic devices that are configured to directly or indirectly communicate with or over one or more networks. The computing device may be a mobile device, a desktop computer, or the like. Furthermore, the term "computer" may refer to any computing device that includes the necessary components to receive, process, and output data, and normally includes a display, a processor, a memory, an input device, and a network interface. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.).

As used herein, the term "server" may refer to or include one or more processors or computers, storage devices, or similar computer arrangements that are operated by or facilitate communication and processing for multiple parties in a network environment, such as the Internet, although it will be appreciated that communication may be facilitated over one or more public or private network environments and that various other arrangements are possible. Further, multiple computers, e.g., servers, or other computerized devices, directly or indirectly communicating in the network environment may constitute a "system". As used herein, the term "data center" may include one or more servers, or other computing devices, and/or databases.

As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices. The terms "client device" and "user device," as used herein, refer to any electronic device that is configured to communicate with one or more servers or remote devices and/or systems. A client device or user device may include a mobile device, a network-enabled appliance (e.g., a network-enabled television, refrigerator, thermostat, and/or the like), a computer, and/or any other device or system capable of communicating with a network.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

Referring to FIG. 1, non-limiting embodiments or aspects of an environment 100 in which systems, devices, products, apparatus, and/or methods, as described herein, may be implemented is shown. As shown in FIG. 1, environment 100 may include flow sensor system 150 including flow sensor 160 and base 180, medical device 102 (e.g., a syringe, etc.) including short range wireless communication tag 104, IV line 106, communications network 108, and/or remote computing device 110.

Medical device 102 may be configured to physically connect to flow sensor 160 as described in more detail herein. Short range wireless communication tag 104 may be attached to or integrated with medical device 102 as described in more detail herein. In some non-limiting embodiments or aspects, short range wireless communication tag 104 includes one or more computing devices, chips, contactless transmitters, contactless transceivers, NFC transmitters/receivers, RFID transmitters/receivers, contact based transmitters/receivers, and/or the like. In some non-limiting embodiments or aspects, short range wireless communication tag 104 can include one or more devices capable of transmitting and/or receiving information to and/or from base 180 via a short range wireless communication connection (e.g., a communication connection that uses NFC protocol, a communication connection that uses Radio-frequency identification (RFID), a communication connection that uses a Bluetooth® wireless technology standard, and/or the like). Further details regarding non-limiting embodiments or aspects of medical device 102 and short range wireless communication tag 104 are provided below with regard to FIGS. 3A-3H, 4A-4D, and 5A-5C.

Flow sensor 160 may be configured to be removably, physically, and/or electrically connected to base 180 as described in more detail herein. In some non-limiting embodiments or aspects, flow sensor 160 may be connected in-line with IV line 106 between a fluid source and a patient. Further details regarding non-limiting embodiments or aspects of flow sensor 160 are provided below with regard to FIGS. 3A-3H, 4A-4D, and 5A-5C.

Base 180 may be configured to be removably, physically, and/or electrically connected to flow sensor 160 as described in more detail herein. Base 180 may include may include one or more devices capable of receiving information and/or data from remote computing device 110 (e.g., via communication network 108, etc.) and/or communicating information and/or data to remote computing device 110 (e.g., via communication network 108, etc.). For example, base 180 may include a computing device, a mobile device, and/or the like. In some non-limiting embodiments or aspects, base 180 includes one or more computing devices, chips, contactless transmitters, contactless transceivers, NFC transmitters/receivers, RFID transmitters/receivers, contact based transmitters/receivers, and/or the like. In some non-limiting embodiments or aspects, base 180 can include one or more devices capable of transmitting and/or receiving information to and/or from short range wireless communication tag 104 via a short range wireless communication connection (e.g., a communication connection that uses NFC protocol, a communication connection that uses Radio-frequency identification (RFID), a communication connection that uses a Bluetooth® wireless technology standard, and/or the like). In some non-limiting embodiments or aspects, base 180 includes an integrated power source (not shown), such as a battery, and/or the like. Further details regarding non-limiting embodiments or aspects of base 180 are provided below with regard to FIGS. 3A-3H, 4A-4D, and 5A-5C.

Communication network 108 may include one or more wired and/or wireless networks. For example, communication network 108 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

Remote computing device 110 may include one or more devices capable of receiving information and/or data from base 180 (e.g., via communication network 108, etc.) and/or communicating information and/or data to base 180 (e.g., via communication network 108, etc.). For example, remote computing device 110 may include a computing device, a server, a group of servers, a mobile device, a group of mobile devices, and/or the like.

The number and arrangement of devices and systems shown in FIG. 1 is provided as an example. There may be additional devices and/or systems, fewer devices and/or systems, different devices and/or systems, or differently arranged devices and/or systems than those shown in FIG. 1. Furthermore, two or more devices and/or systems shown in FIG. 1 may be implemented within a single device and/or system, or a single device and/or system shown in FIG. 1 may be implemented as multiple, distributed devices and/or systems. Additionally, or alternatively, a set of devices and/or systems (e.g., one or more devices or systems) of environment 100 may perform one or more functions described as being performed by another set of devices and/or systems of environment 100.

Figure 2:
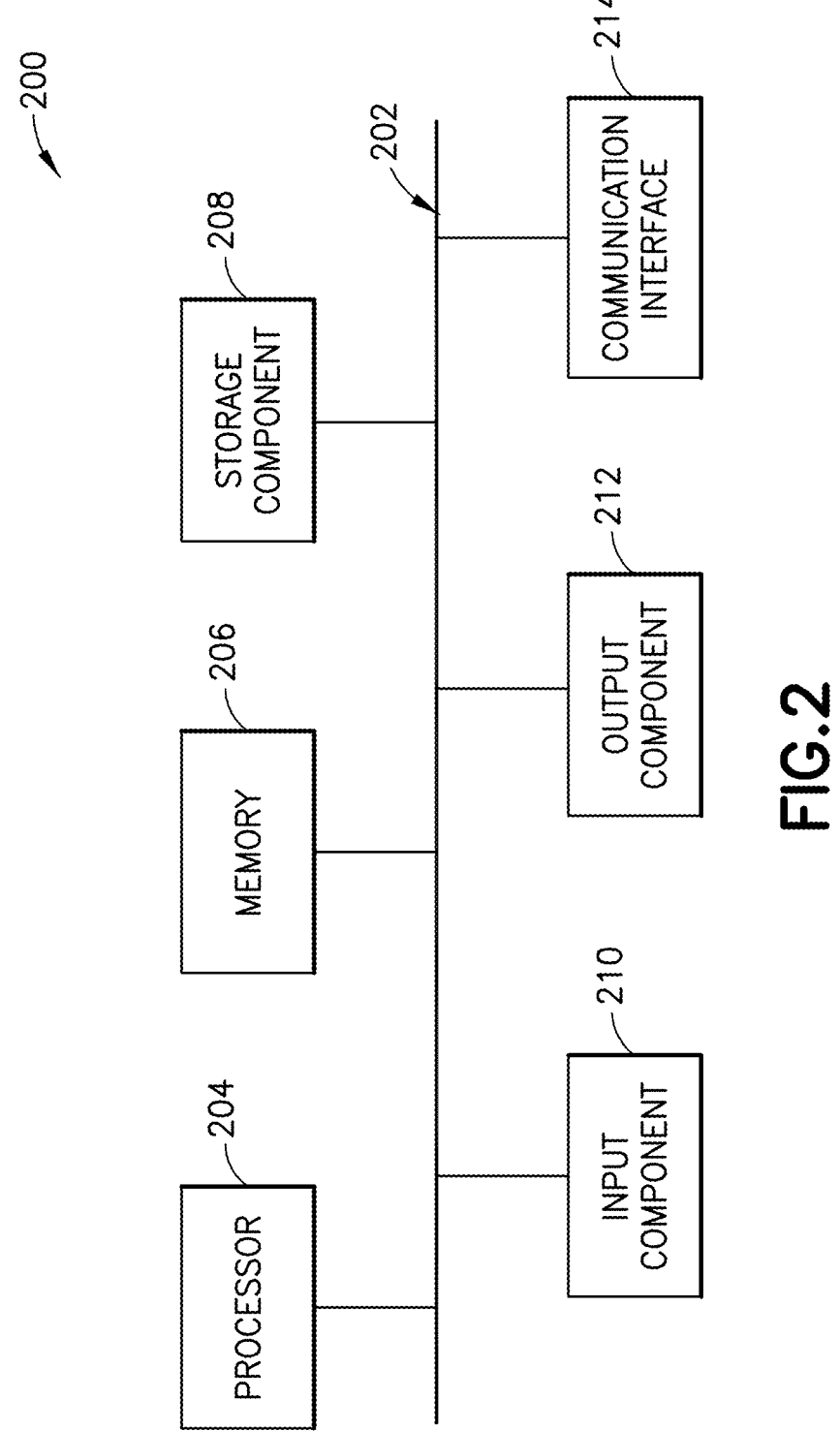
FIG. 2 is a diagram of non-limiting embodiments or aspects of components of one or more devices and/or one or more systems of FIG. 1.
Figure 3A:
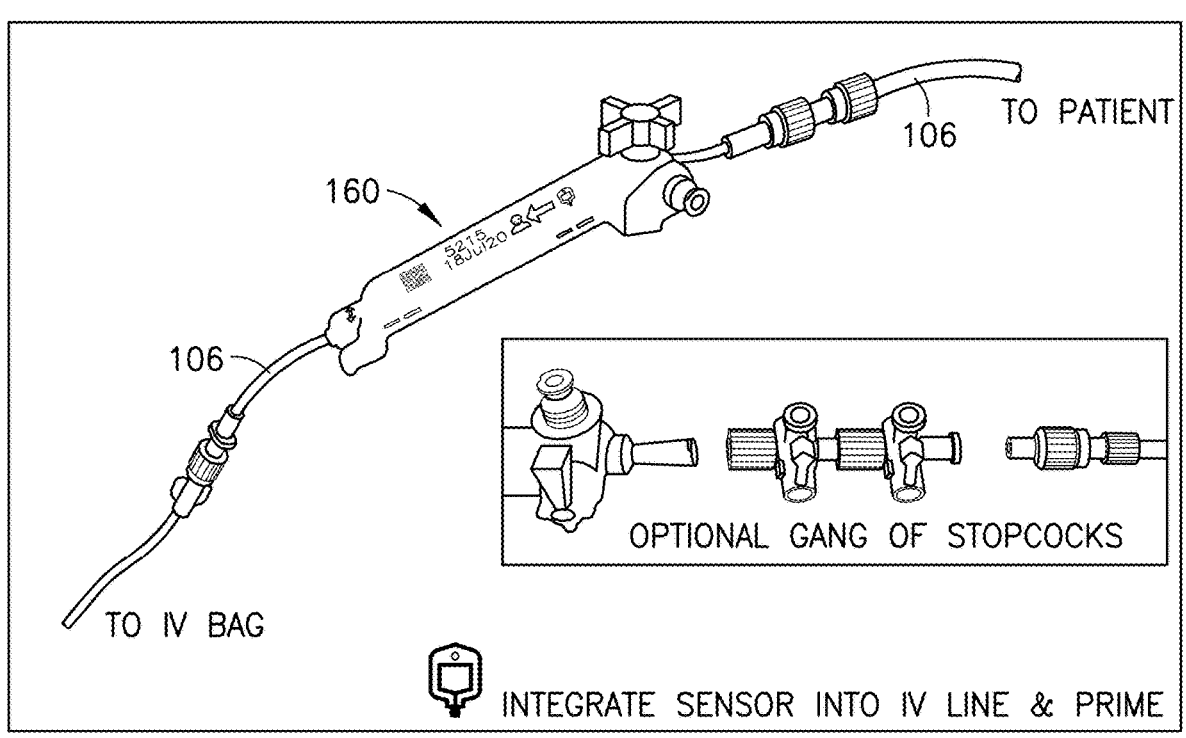
FIG. 3A is a flow chart of a non-limiting embodiment or aspect of a process for using a flow sensor system.
Figure 3B:
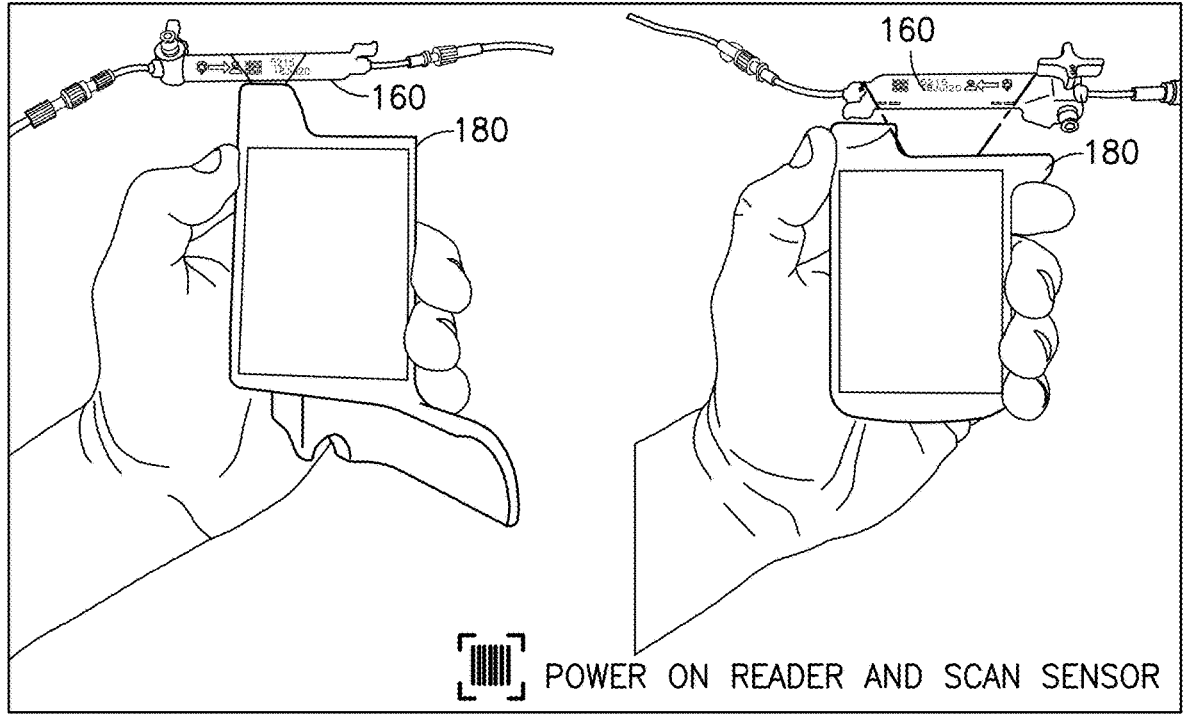
FIG. 3B is a flow chart of a non-limiting embodiment or aspect of a process for using a flow sensor system.
Figure 3C:
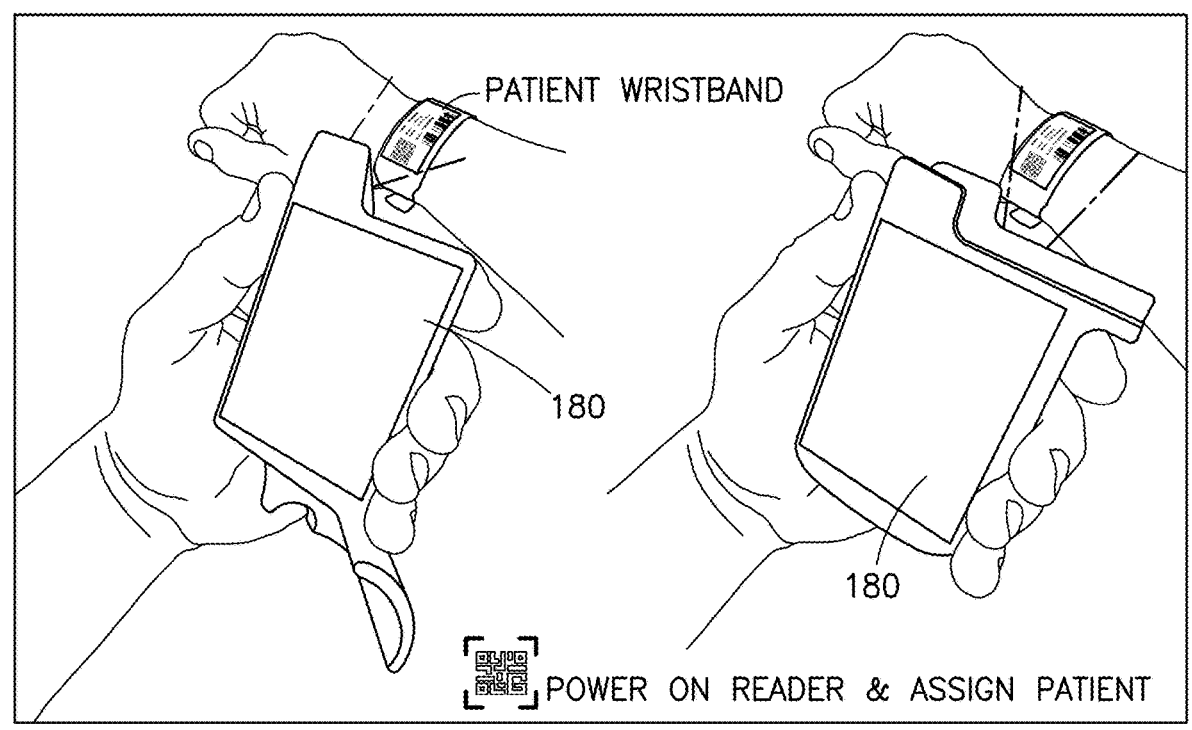
FIG. 3C is a flow chart of a non-limiting embodiment or aspect of a process for using a flow sensor system.
Figure 3D:
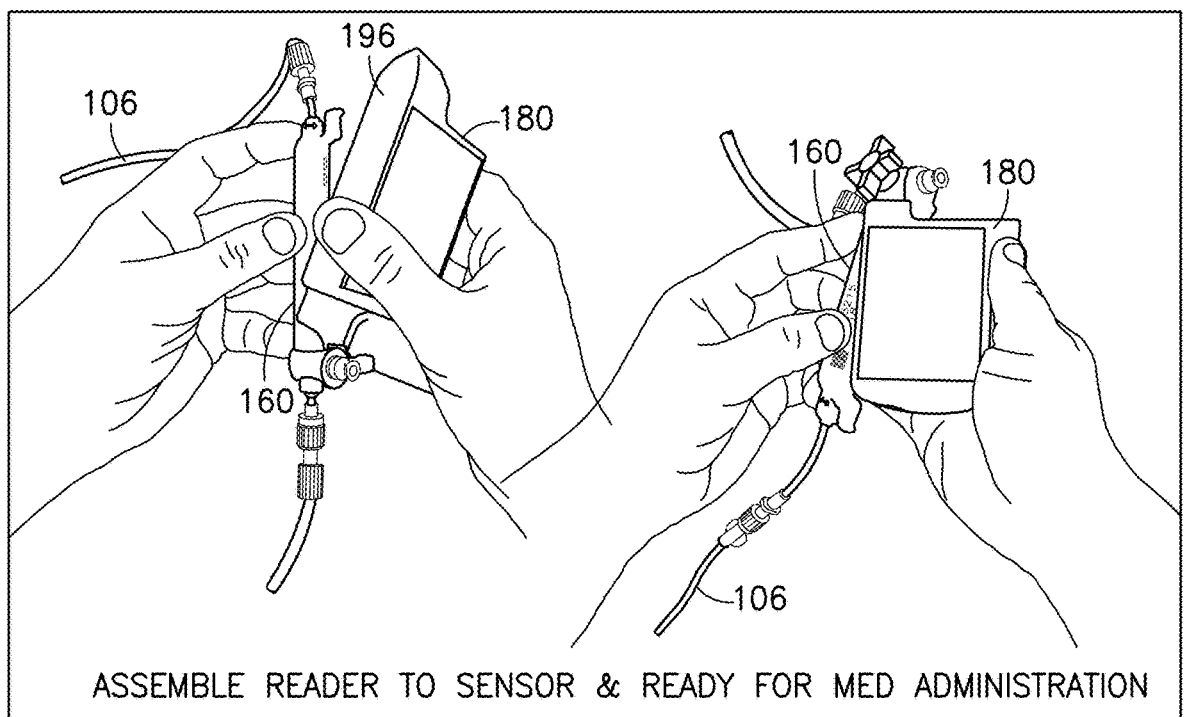
FIG. 3D is a flow chart of a non-limiting embodiment or aspect of a process for using a flow sensor system.
Figure 3E:
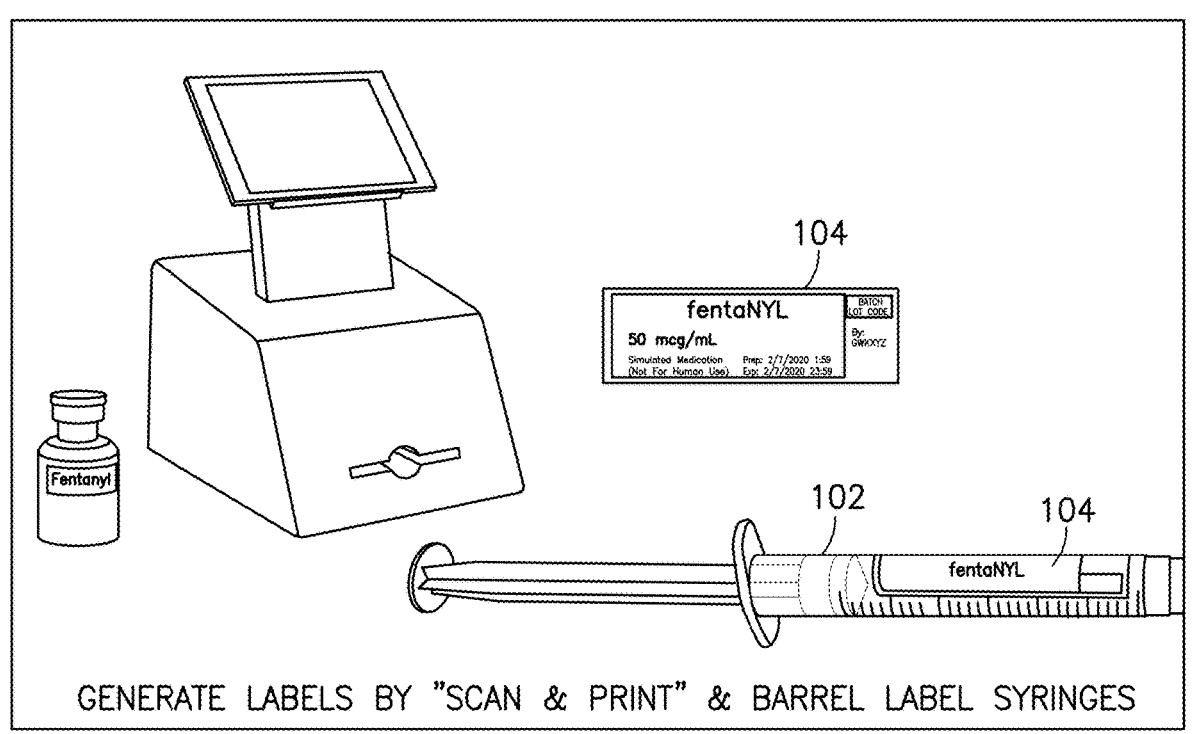
FIG. 3E is a flow chart of a non-limiting embodiment or aspect of a process for using a flow sensor system.
Figure 3F:
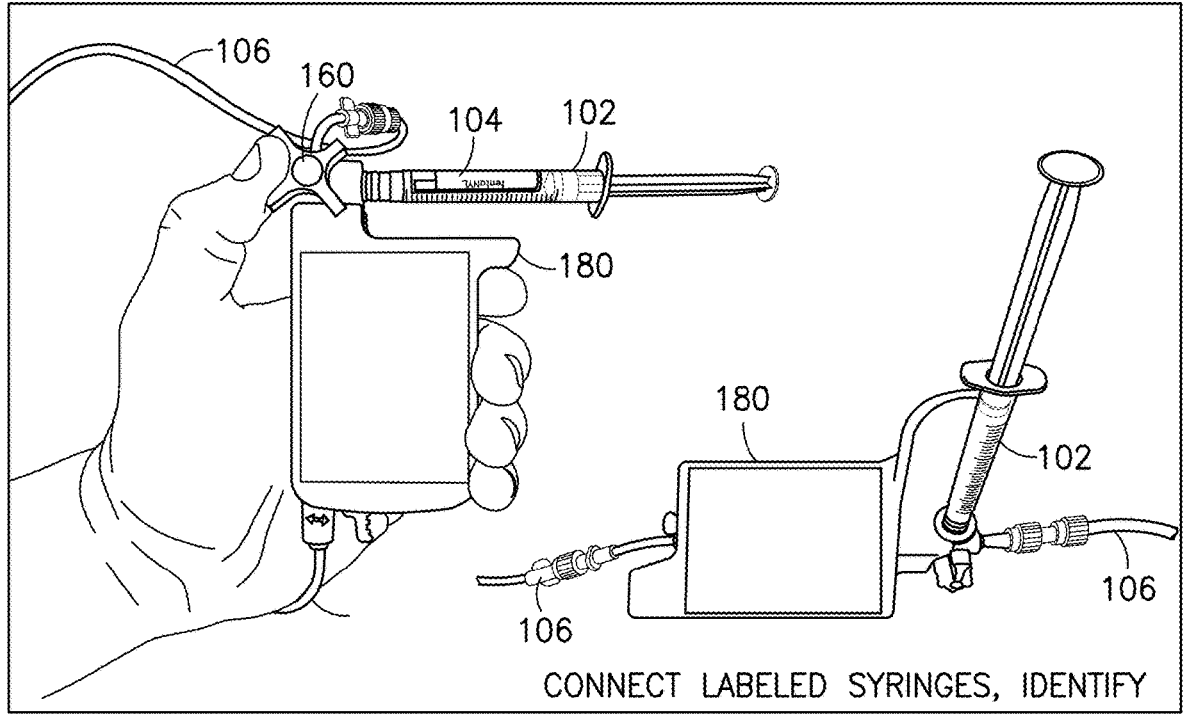
FIG. 3F is a flow chart of a non-limiting embodiment or aspect of a process for using a flow sensor system.
Figure 3G:
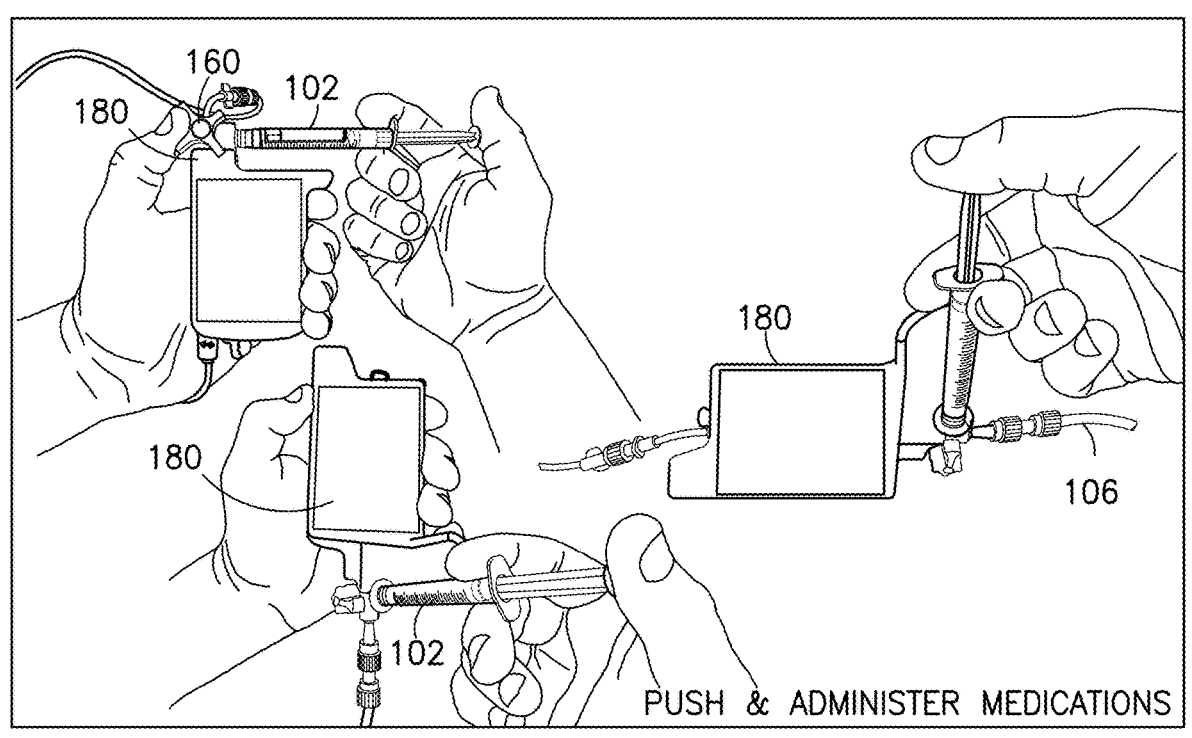
FIG. 3G is a flow chart of a non-limiting embodiment or aspect of a process for using a flow sensor system.
Figure 3H:
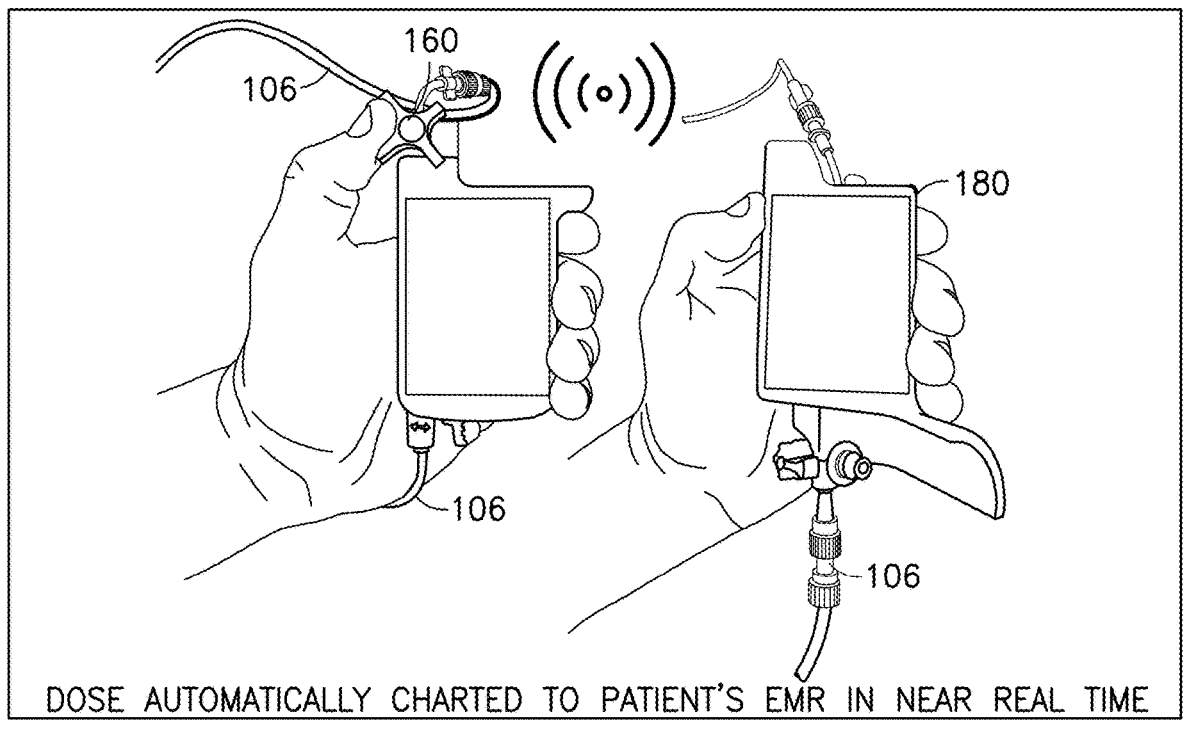
FIG. 3H is a flow chart of a non-limiting embodiment or aspect of a process for using a flow sensor system.
Figure 4A:
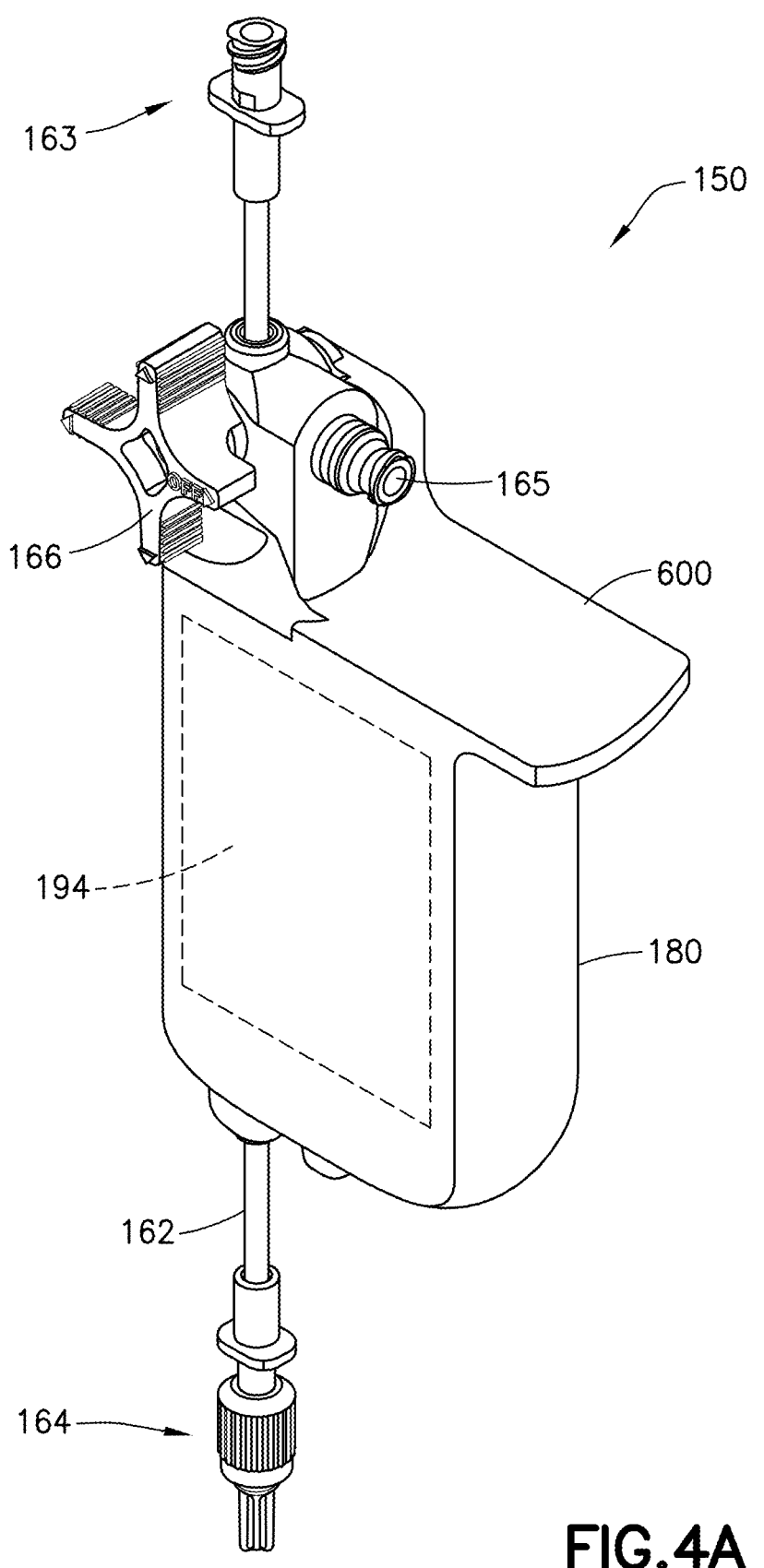
FIG. 4A is a perspective view of an implementation of non-limiting embodiments or aspects of a flow sensor system.
Figure 4B:
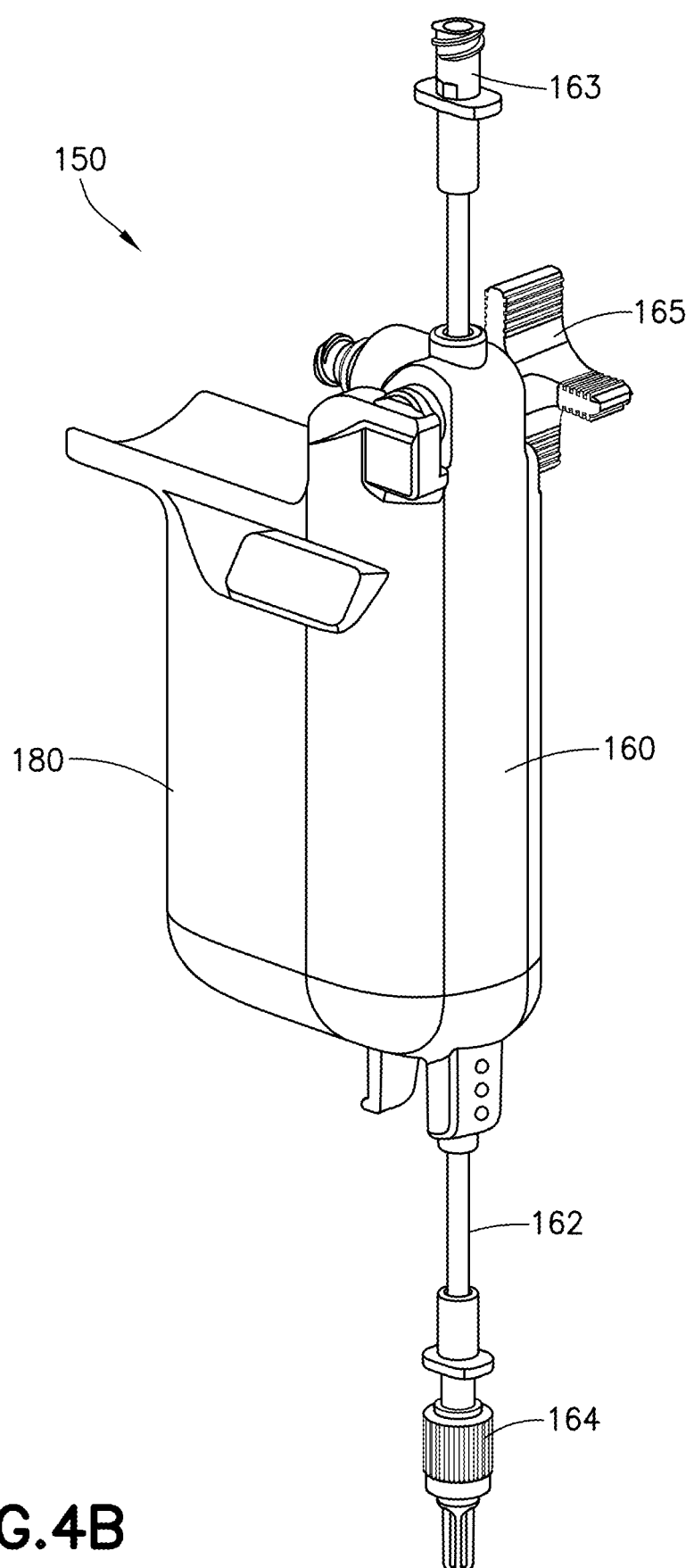
FIG. 4B is a perspective view of an implementation of non-limiting embodiments or aspects of a flow sensor system.
Figure 4C:
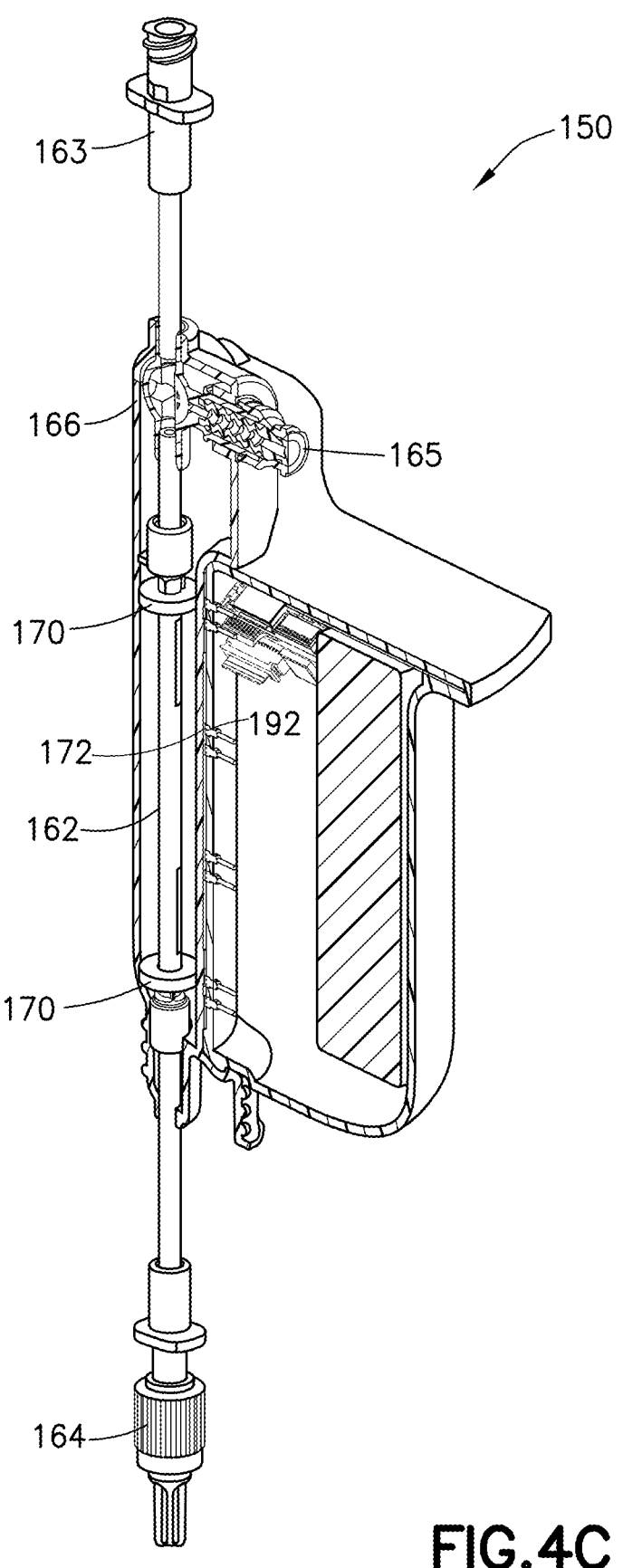
FIG. 4C is a perspective view of an implementation of non-limiting embodiments or aspects of a flow sensor system.
Figure 4D:
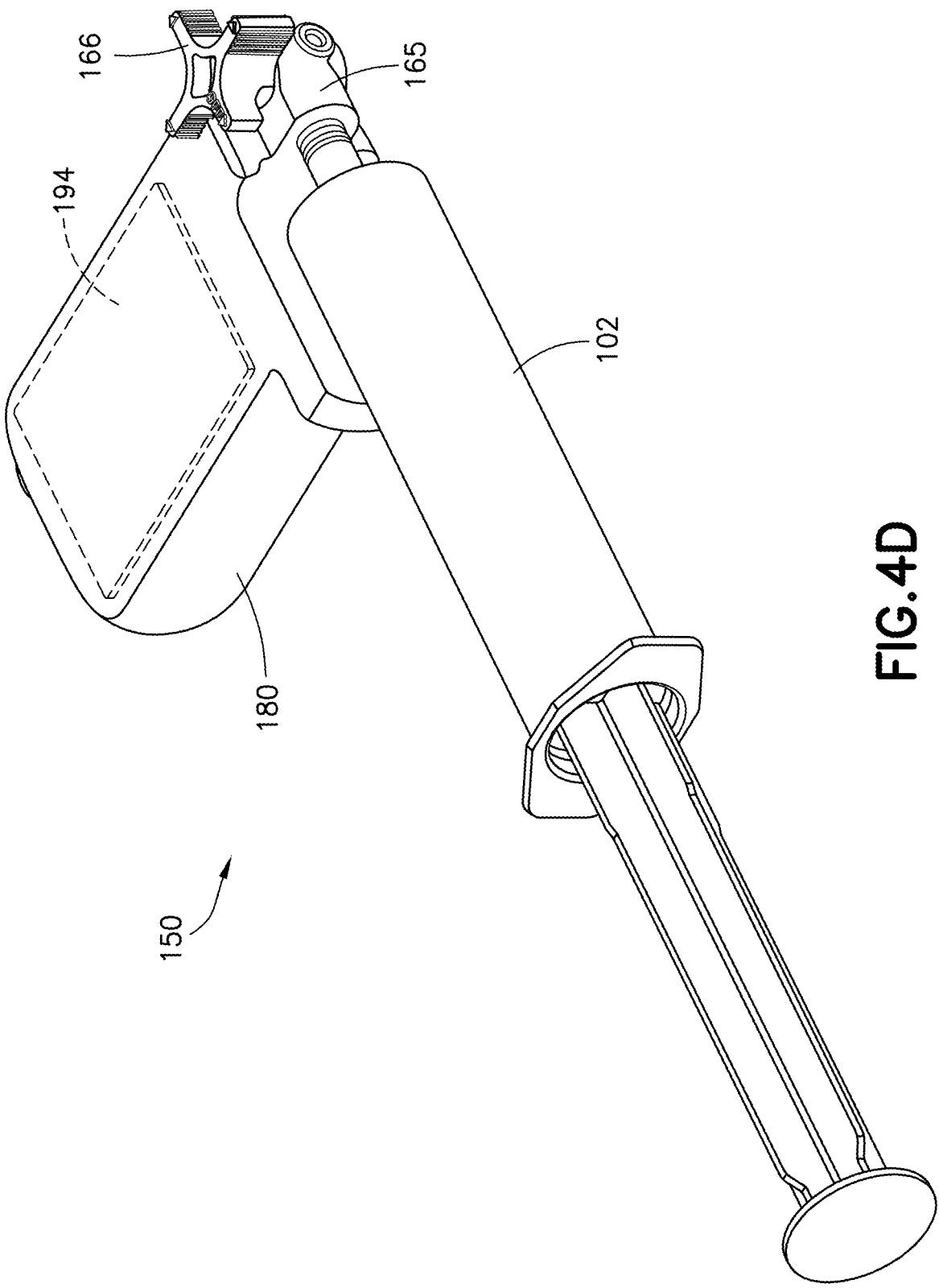
FIG. 4D is a perspective view of an implementation of non-limiting embodiments or aspects of a flow sensor system.
Figure 5A:
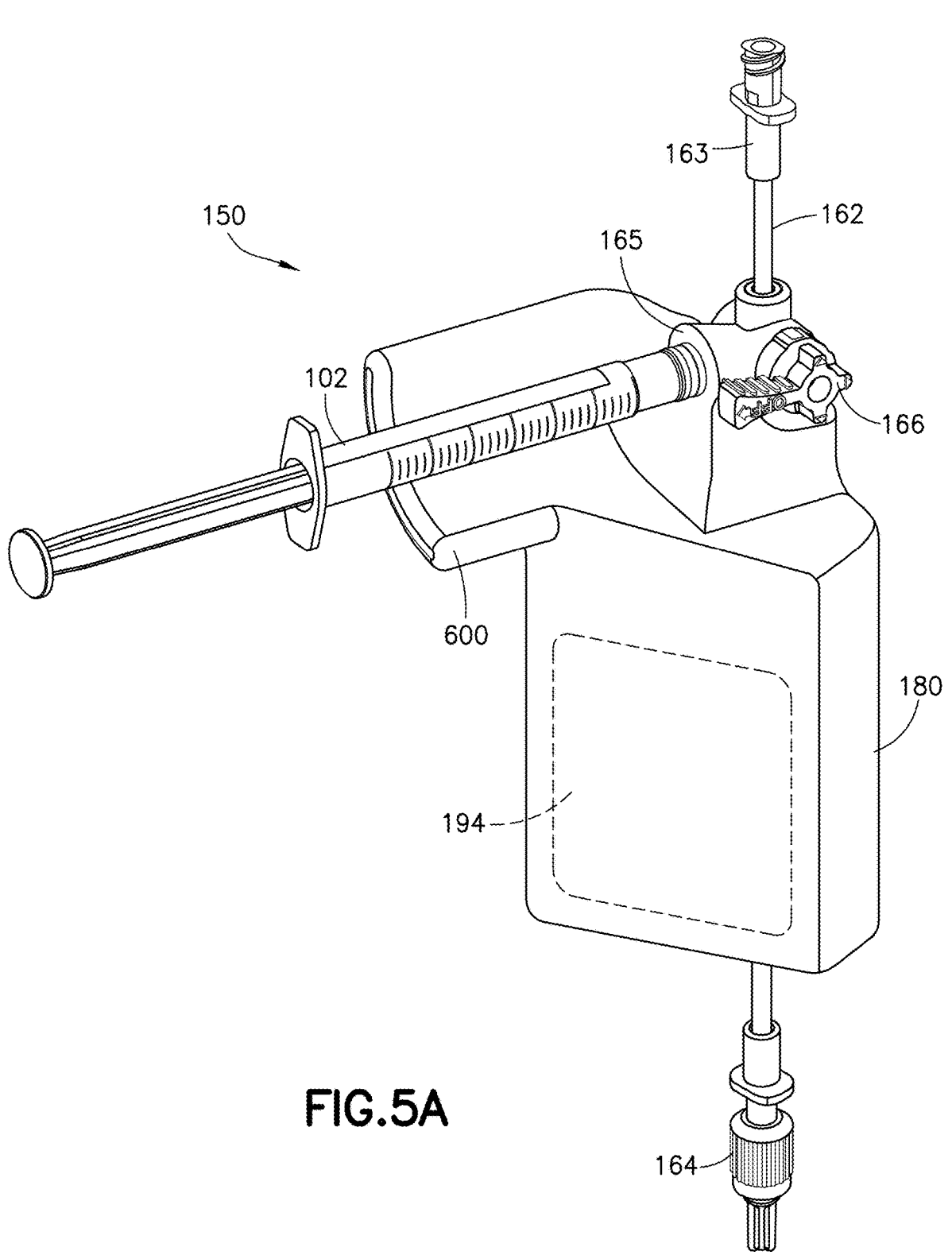
FIG. 5A is a perspective view of an implementation of non-limiting embodiments or aspects of a flow sensor system.
Figure 5B:
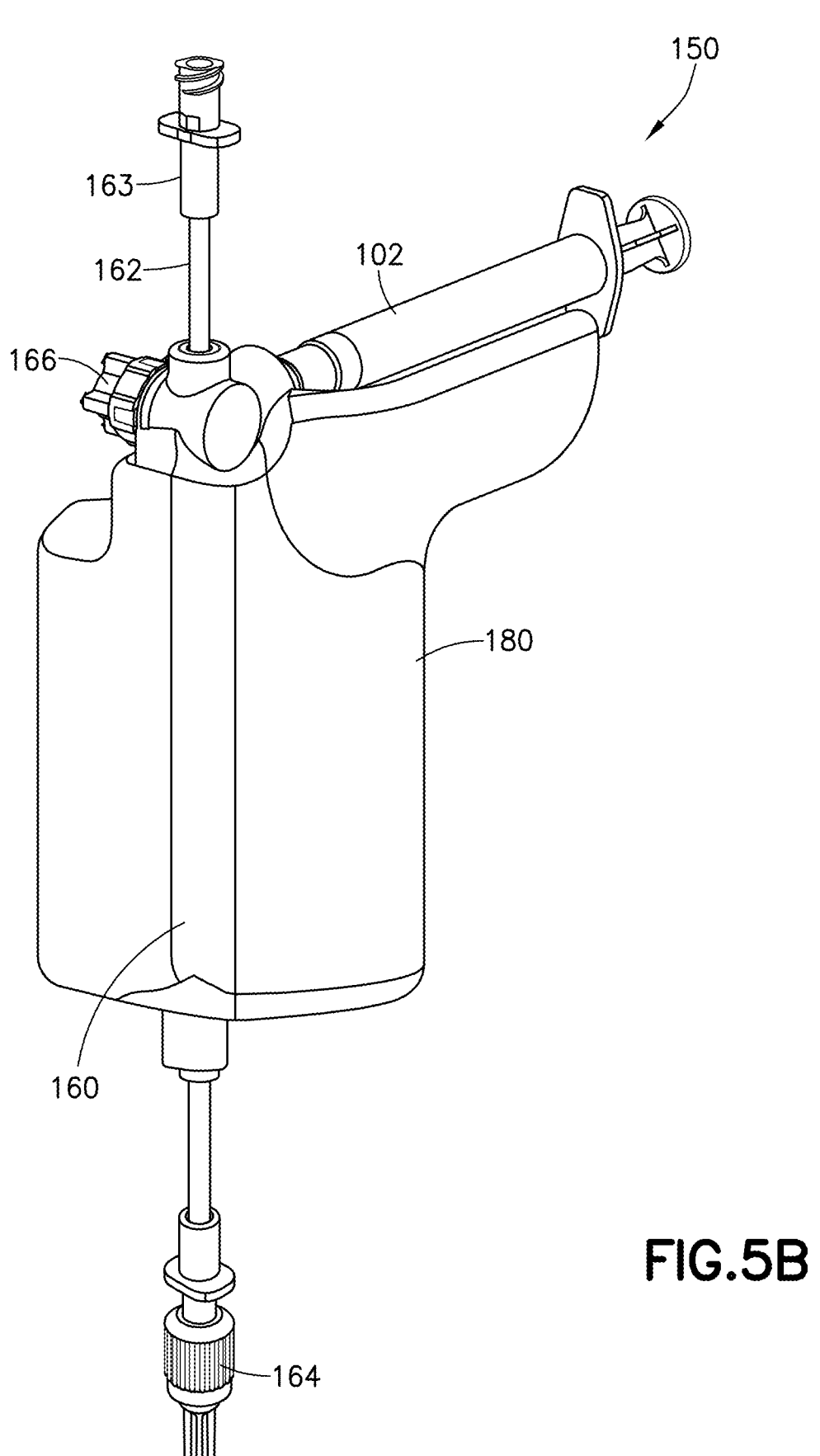
FIG. 5B is a perspective view of an implementation of non-limiting embodiments or aspects of a flow sensor system.
Figure 5C:
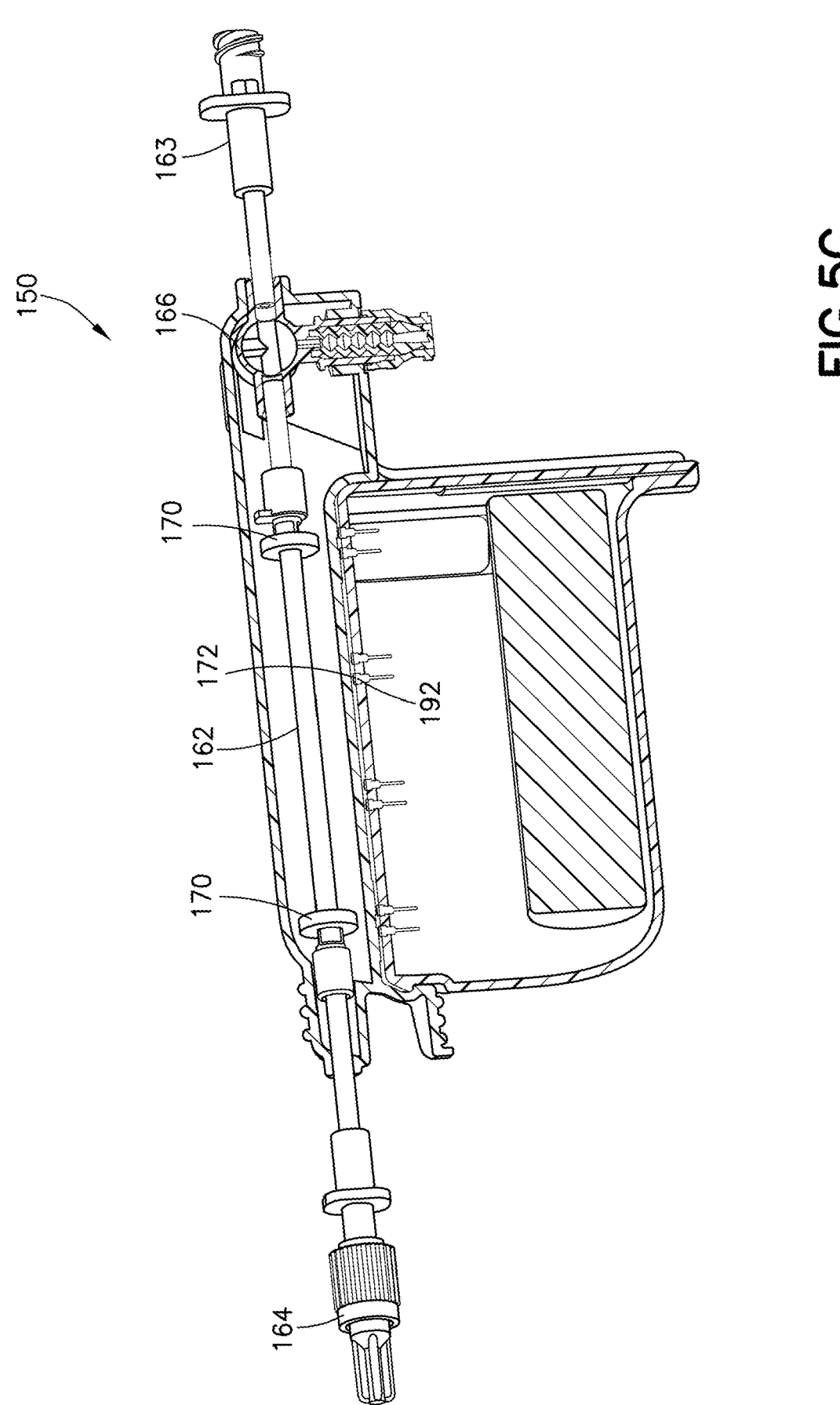
FIG. 5C is a perspective view of an implementation of non-limiting embodiments or aspects of a flow sensor system.
Figure 6A:
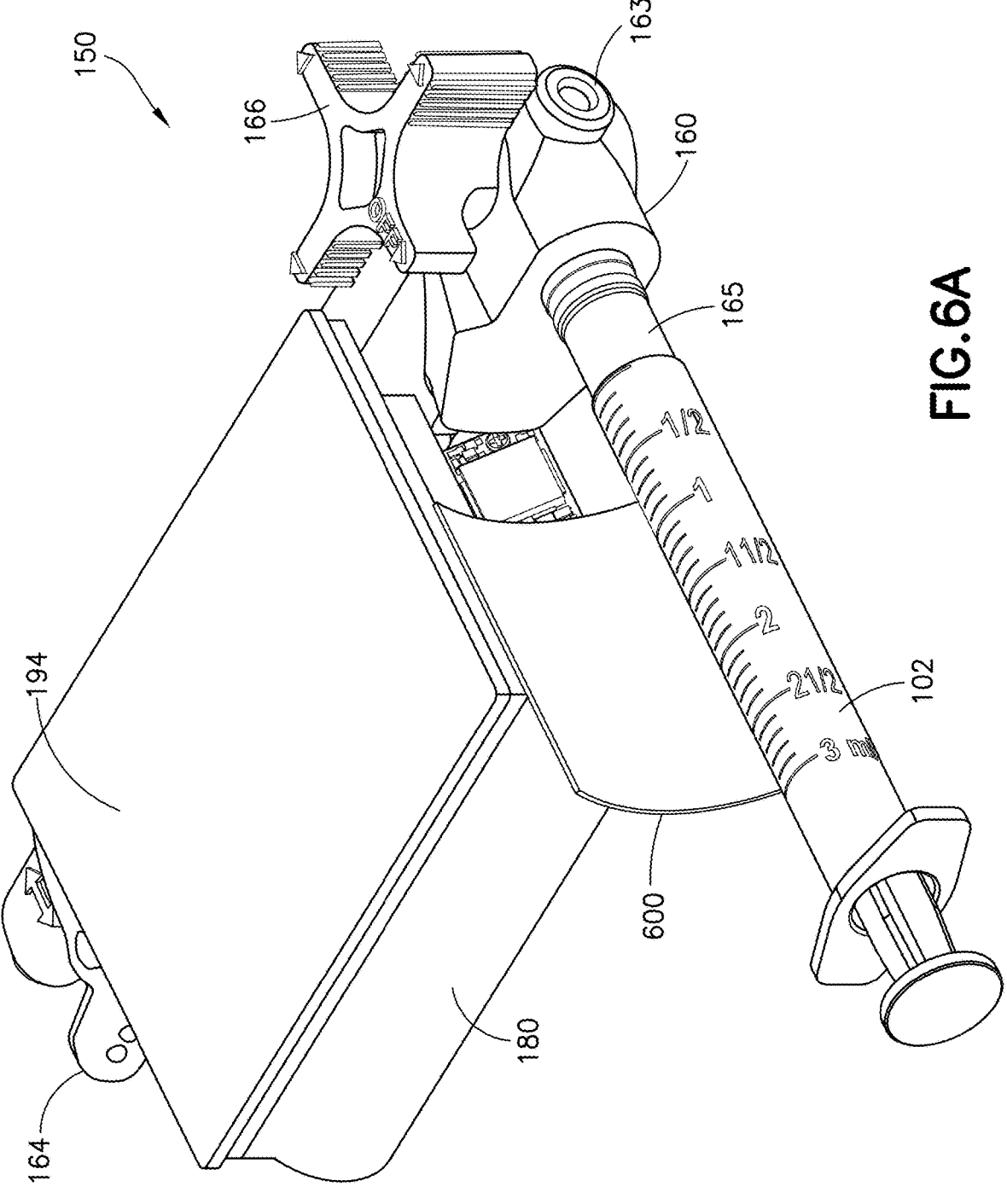
FIG. 6A is a perspective view of an implementation of non-limiting embodiments or aspects of a flow sensor system.
Figure 6B:
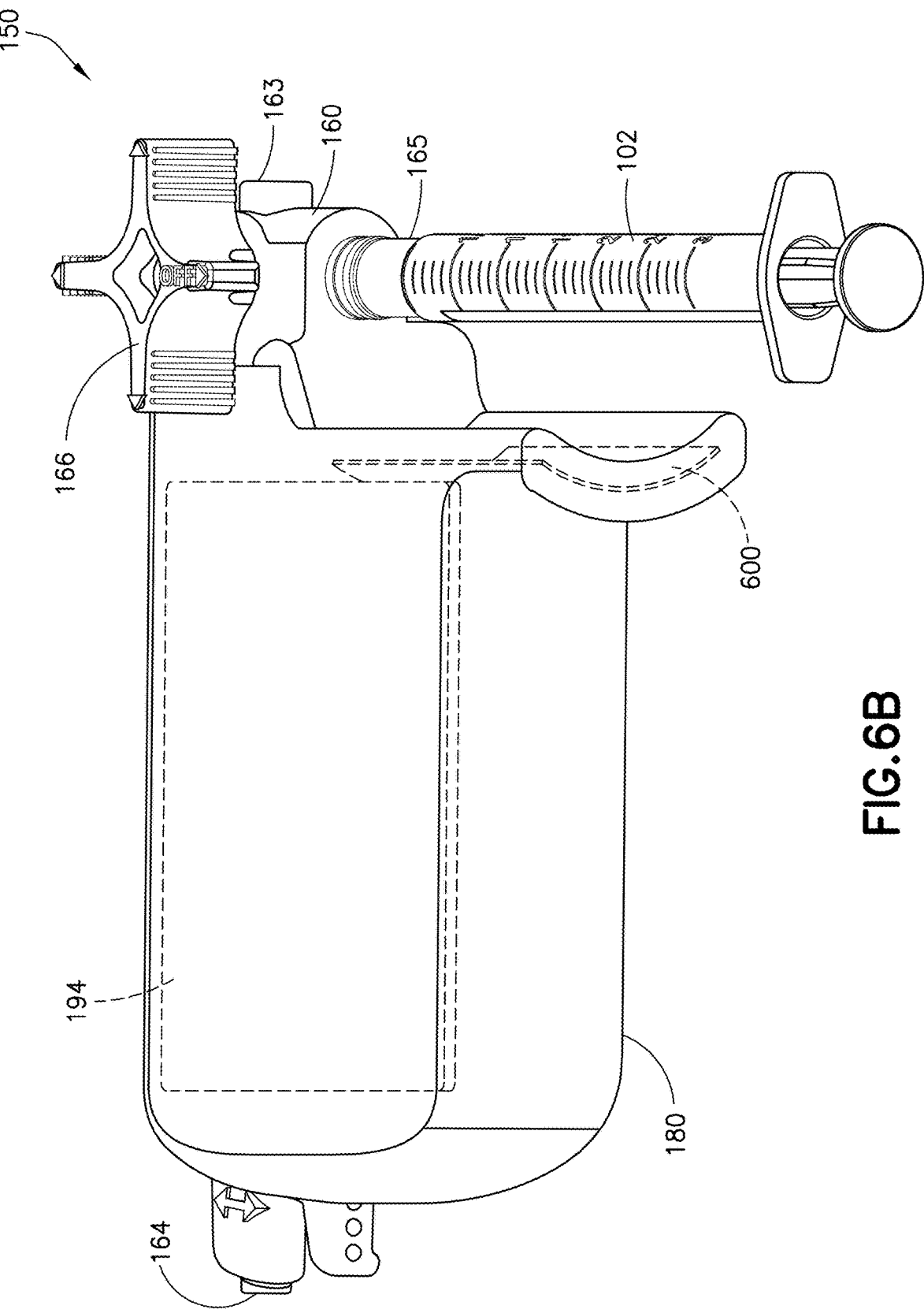
FIG. 6B is a perspective view of an implementation of non-limiting embodiments or aspects of a flow sensor system.
Figure 6C:
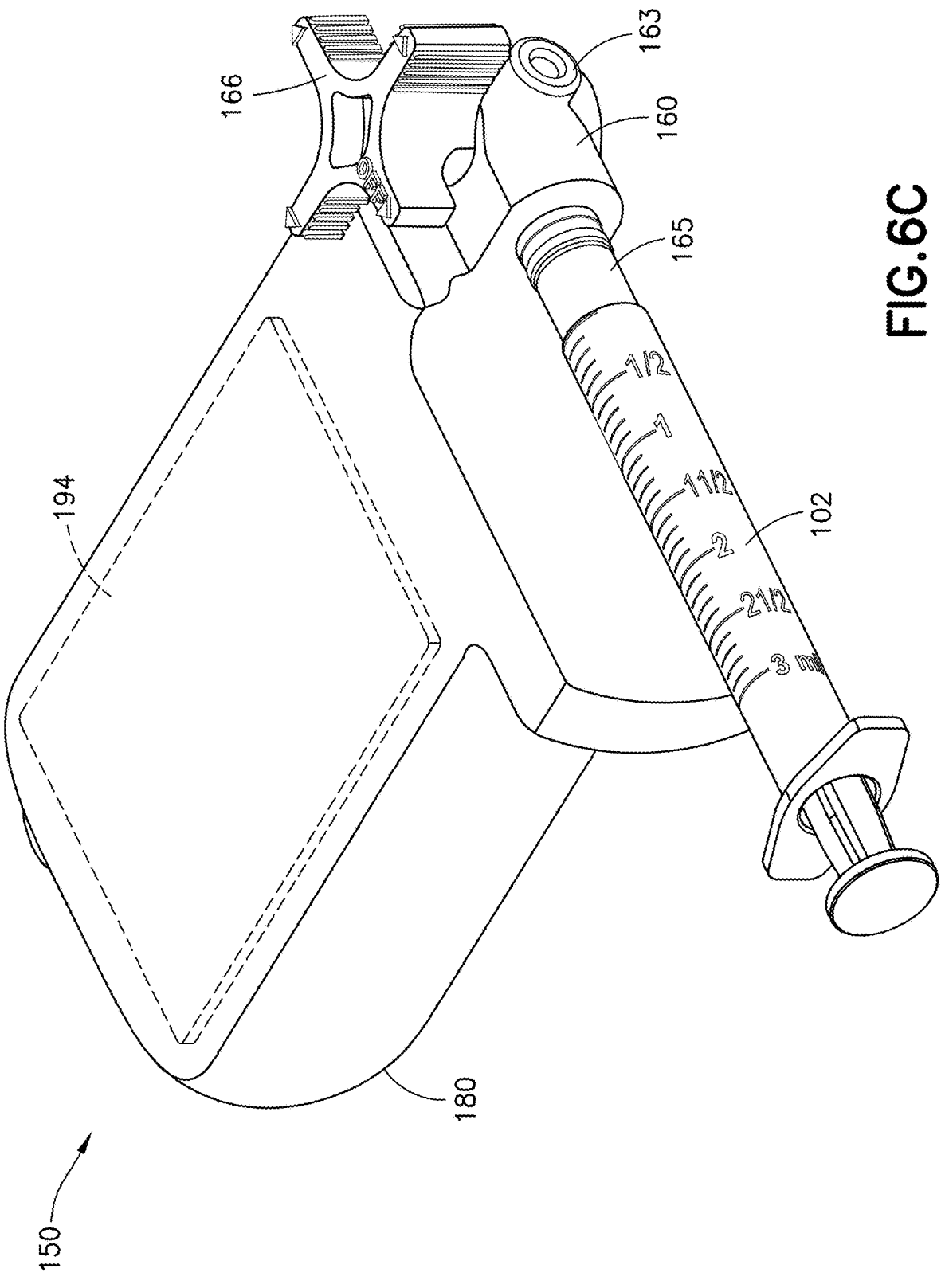
FIG. 6C is a perspective view of an implementation of non-limiting embodiments or aspects of a flow sensor system.
Figure 7A:
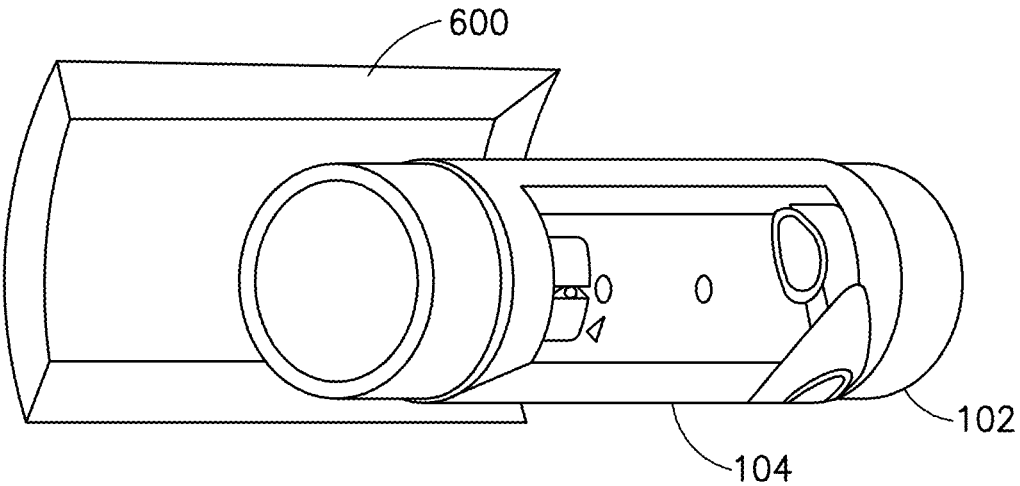
FIG. 7A is a perspective view of an implementation of non-limiting embodiments or aspects of a flow sensor system.
Figure 7B:
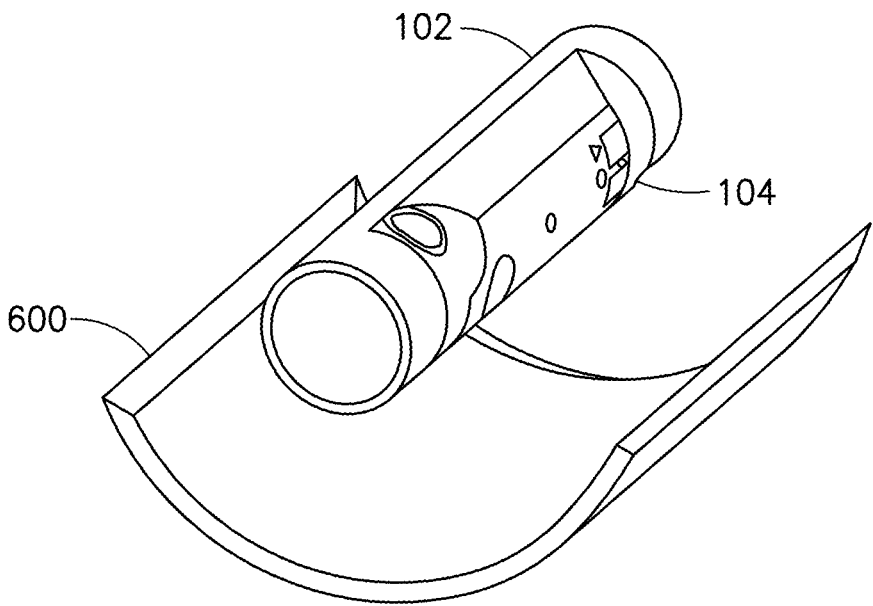
FIG. 7B is a perspective view of an implementation of non-limiting embodiments or aspects of a flow sensor system.
Figure 8:
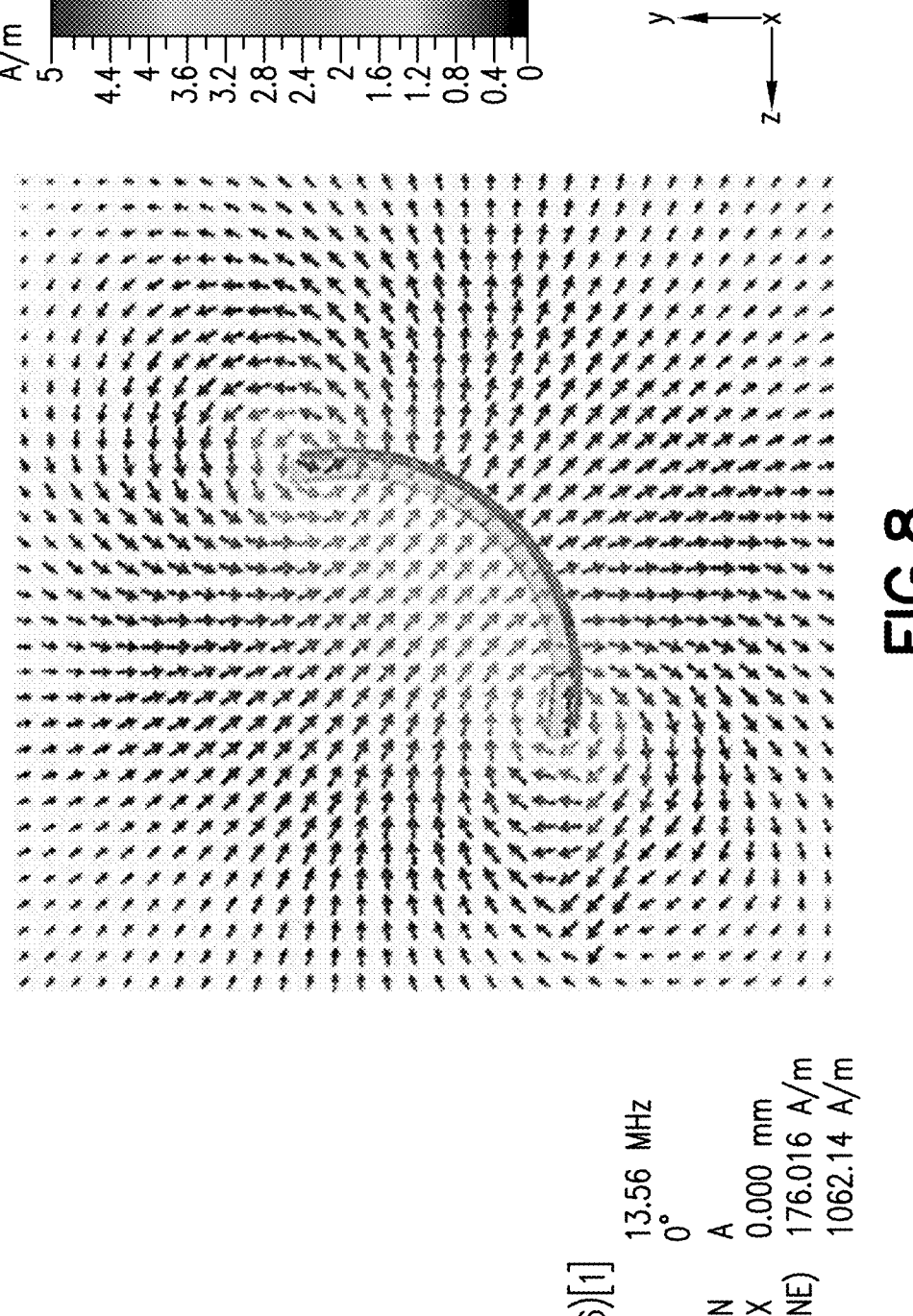
FIG. 8 is a diagram of an example magnetic H-field around an antenna of a flow sensor system according to non-limiting embodiments or aspects.

Referring now to FIG. 2, FIG. 2 is a diagram of example components of a device 200. Device 200 may correspond to base 180 and/or remote computing device 110. In some non-limiting embodiments or aspects, base 180 and/or remote computing device 110 may include at least one device 200 and/or at least one component of device 200. As shown in FIG. 2, device 200 may include bus 202, processor 204, memory 206, storage component 208, input component 210, output component 212, and/or communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.), and/or the like, which can be programmed to perform a function. Memory 206 may include a random-access memory (RAM), a read only memory (ROM), and/or another type of dynamic or static storage device (e.g., a flash memory, a magnetic memory, an optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, an NFC sensor, an RFID sensor, an optical sensor, a bar code reader, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmission source, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

FIGS. 3A-3H, 4A-4D, and 5A-5C illustrate non-limiting embodiments or aspects of flow sensor system 150. Referring to FIGS. 3A-3H, 4A-4D, and 5A-5C, flow sensor system 150 may include two main assemblies which fit together prior to use: flow sensor 160 and base 180. In some non-limiting embodiments or aspects, flow sensor 160 may be a single-use flow sensor which is engageable with reusable base 180.

Flow sensor system 150 may reduce medication error at bedside during bolus delivery. Flow sensor system 150 may provide a record of and electronically measure bolus delivery, which allows monitoring bolus delivery and automatic documentation of bolus delivery as part of a patient's health record. Flow sensor system 150 may provide alerts when bolus delivery inconsistent with a patient's medical record is about to occur.

Flow sensor system 150 may be a handheld instrument Injection Site with interactive interface for syringe injection IV drug delivery and direct electronic medical record documentation. Base 180 may include a durable reusable reader base with a touchscreen display and a separate disposable consumable flow sensor 160.

In some non-limiting embodiments or aspects, flow sensor 160 may include a flow tube 162, at least one sensor 170 configured to characterize at least one attribute of the fluid in the flow tube 162, and/or a flow senor electrical contact 172 in electrical communication with the at least one sensor 170. The flow tube 162 may include a fluid inlet 163 at a first end of the flow tube 162, a fluid outlet 164 at a second end of the flow tube 162 opposite the first end of the flow tube 162, a fluid injection port 165 between the first end and the second end of the flow tube 162, and a valve 166 (e.g., a manual valve, etc.) configured to control a flow of a fluid in the flow tube 162.

In some non-limiting embodiments or aspects, base 180 may include one or more processors 204, a base electrical contact 192 in electrical communication with the one or more processors 204, a short range wireless communication device (e.g., communication interface 214, a near-field communication (NFC) receiver, etc.), and/or a display 194 (e.g., input component 210, output component 212, a touchscreen display configured to receive user input from a user, etc.). The flow sensor electrical contact 172 may be in electrical communication with the base electrical contact 192 when the flow sensor is connected (e.g., connected, attached, mounted, etc.) to the base 180.

In some non-limiting embodiments or aspects, base 180 includes an opening 196 configured to receive the flow sensor 160, and the flow sensor 160 is configured for sliding engagement with the opening 196 of the base 180.

In some non-limiting embodiments or aspects, the at least one sensor 170 may include a first ultrasonic transducer or piezo element 170 arranged at an upstream position of the flow tube 162 and a second ultrasonic transducer or piezo element 170 is arranged at a downstream position of the flow tube 162. The first and second piezo elements 170 may be configured to transmit a flow signal indicative of a flow of a fluid (e.g., a fluidic medicament, etc.) in the flow tube 162. In some non-limiting embodiments or aspects, the first ultrasonic transducer or piezo element and the second ultrasonic transducer or piezo element 170 are annular in shape and encircle the flow tube 162 at respective mounting points. In some non-limiting embodiments or aspects, the first ultrasonic transducer or piezo element and the second ultrasonic transducer or piezo element 170 are mounted apart a pre-selected distance from each other. The first and second ultrasonic transducers or piezeo elements 170 may be in electrical communication with the one or more processors 204 (e.g., via the electrical contacts 172, 192, etc.) when the flow sensor 160 is connected to the base 180. For example, base 180 may interact with the first and second ultrasonic transducers or piezeo elements 170 in flow sensor 160 to measure displacement of fluid through the flow sensor 160.

In some non-limiting embodiments or aspects, valve 166 may be configured transition between a plurality of different states to control at least one of: the flow of the fluid between the fluid inlet 163 and the fluid outlet 164, the flow of the fluid between the fluid inlet 163 and the fluid injection port 165, the flow of the fluid between the fluid injection port 165 and the fluid outlet 164, or any combination thereof. For example, valve 166 may include a 3-way stopcock valve, and/or the like.

In some non-limiting embodiments or aspects, the one or more processors 204 may be programmed and/or configured to automatically detect a connection of flow sensor 160 to base 180. For example, when a user attaches flow sensor 160 to reader base 180, reader base 180 automatically detects flow sensor 160 installation. As an example, a mechanical button or switch on base 180 in electrical communication with the one or more processors may be actuated by connection/disconnection of flow sensor 160 to base 180 to send a signal to the one or more processors 204 indicating the connection/disconnection state of flow sensor 160 to base 180.

In some non-limiting embodiments or aspects, the one or more processors 204 are programmed and/or configured to automatically detect a connection of a syringe 102 to the fluid injection port 165 of the flow sensor 160. For example, when a user inserts a syringe 102 with needle free Luer connector into fluid injection port 165, reader base 180 may automatically detect the connection of the syringe to the fluid injection port 165 syringe presence and initiates decoding of tag 104 (e.g., via the short range wireless communication device, etc.) to record information contents of tag 104 (e.g., medication information, etc.). As an example, flow sensor system 150 may include an electronic and mechanical interface that interacts with the syringe 102 when inserted into fluid injection port 165 to detect the presence of the syringe 102 upon insertion by the user. In such an example, a mechanical button or switch on flow sensor 160 in electrical communication with the one or more processors (e.g., via the electrical contacts 172 and 192, etc.) may be actuated by connection/disconnection syringe 102 to fluid injection port 165 to send a signal to the one or more processors 204 indicating the connection/disconnection state of syringe 102 to fluid injection port 165. In some non-limiting embodiments or aspects, tag or label 104, which may include an NFC tag embedded in the tag or label 104, may be manually placed on a body of syringe 102 using a standard label printer. For example, a label printer can be used to encode the NFC tag at the time of printing. Additionally or alternatively, NFC encoding can be performed using a separate NFC tag encoding unit.

In some non-limiting embodiments or aspects, the short range wireless communication device is configured to automatically communicate with the short range wireless communication tag 104 on syringe 102 via a short range wireless communication connection when the short range wireless communication tag 104 is brought within a communication range of the short range wireless communication device. In some non-limiting embodiments or aspects, the short range wireless communication device is configured to automatically communicate with the short range wireless communication tag 104 on the syringe 102 via a short range wireless communication connection in response to the base 180 detecting a connection of the syringe 102 to the fluid injection port 165. For example, the tag 104 may be detected by using NFC when placed radially adjacent to an antenna of the short range wireless communication device in base 180. As an example, base 180 may include an integrated NFC antenna positioned radially to record syringe label tag 104 and read and decode encoded information therefrom. In such an example, the NFC antenna and label tags are optimized to eliminate false detection of adjacently positioned syringes with NFC tag labels (e.g., an NFC antenna mounted radially in the base 180 and label tag 104 on the syringe barrel of syringe 102 can be used to transmit encoded label information from the syringe label tag 104 to the reader base 180, etc.).

In some non-limiting embodiments or aspects, the one or more processors 204 may be programmed and/or configured to automatically detect a state of the valve 166 when the flow sensor 160 is connected to the base 180. For example, base 180 may automatically determine a state or position of valve 166 when a user manually switches the state or position of the valve 166. As an example, an electronic and/or mechanical interface may interact with the valve 166 to monitor valve position or state. In such an example, a mechanical button or switch on flow sensor 160 in electrical communication with the one or more processors (e.g., via the electrical contacts 172 and 192, etc.) may be actuated by changing the position or state of the valve 166 to send a signal to the one or more processors 204 indicating the state or position of the valve 166 (e.g., indicating that fluid flow is allowed between the fluid inlet 163 and the fluid outlet 164, between the fluid inlet 163 and the fluid injection port 165, between the fluid injection port 165 and the fluid outlet 164, or any combination thereof, etc.).

In some non-limiting embodiments or aspects, the one or more processors 204 are programmed and/or configured to determine whether to record information associated with the at least one attribute of the fluid in the flow tube 162 based on the detected state of the valve 166. For example, a user may switch the state or position of the valve 166 to enable recording of flow measurement and/or permit IV fluid flow. As an example, the one or more processors 204 of base 180 may determine when to bookmark flow measurements and ignore IV fluid flow and redundant volume measurements when IV fluid is drawn into the syringe 102 then subsequently injected through the flow sensor 160.

In some non-limiting embodiments or aspects, flow sensor 160 is inserted in-line with IV line 106 between a fluid source and a patient. For example, disposable flow sensor 160 can be inserted in-line with IV line 106 enabling IV fluid to pass directly to a patient extension line catheter. In some non-limiting embodiments or aspects, valve 166 is configured to enable syringe 102 to draw IV fluid from IV line 106 and deliver the drawn IV fluid through the flow sensor 160 to push the fluid to flush the flow sensor 160 and extension line of a previously delivered drug volume. In some non-limiting embodiments or aspects, flow sensor 160 may be integrated into IV 106 (e.g., into an IV extension set line, etc.) without separate detachable connectors. In some non-limiting embodiments or aspects, fluid flow stopcock valves can be positioned in-line before and/or after flow sensor 160 and/or additional functionality to incorporate workflow operations can be developed within the interactive display 194 of base 180. For example, by positioning flow sensor 160 in-line with IV line 106, a dead space issue to due lack of flushing associated with parallel connections can be resolved.

In some non-limiting embodiments or aspects, base 180 includes an optical scanner configured to read a bar code label (e.g., a patient wristband bar code label, a bar code label on flow sensor 160, etc.).

In some non-limiting embodiments or aspects, display 194 includes a touchscreen display configured to receive user input from a user. For example display 194 may include an interactive graphical user interface configured to display a current status of internal functions of reader base 180, a current status of an injection site, and/or a prompt for user interaction, and reader base 180 may interact with the user via touchscreen display, audio, voice command, haptic feedback, and/or the like (e.g., to prompt the user on current status and request user input, etc.). Accordingly, by incorporating display 194 into base 180, a user need not remove their attention from the base 180 to interact with the display 194.

In some non-limiting embodiments or aspects, base 180 includes a wireless communication device configured to communicate information associated with the at least one attribute of the fluid in the flow tube 162 to remote computing device 110. For example, base 180 may communicate information and/or data with remote computing device 110 to document drug delivery occurrences into patient medical records (e.g., patient medical records associated with a patient wristband bar code label scanned by the optical scanner of base 180, etc.).

Referring now to FIGS. 4A, 5A, 6A-6C, 7A, 7B, and 8, in some non-limiting embodiments or aspects, short range wireless communication device of base 180 may include a curved coil antenna 600.

A size of syringe 102 may vary (e.g., a syringe size may be in a range from 1 mL to 60 mL, etc.). A location of short range wireless communication tag 104 on syringe 102 may vary. For example, a user may attach short range wireless communication tag 104 at various different locations on a body of syringe 102. The variability between location of the tag 104 and the size of the syringe 102 in combination with a curvature of the body syringe 102 may make reading encoded data off of tag 104 more difficult and/or put considerable burden on a user. For example, HF RFID/NFC works by creating an inductive coupling of magnetic waves in the 13.56 MHz range to power up a HF RFID/NFC tag, which transmits the encoded information back to a transmitting coil antenna. As an example, the transmitting coil antenna should transmit enough energy to power up the tag 104, and a tag coil antenna in tag 104 should receive enough energy to power up and transmit the encoded information stored in tag 104 back to the transmitting coil antenna. A transmitting coil antenna may be flat and the tag 104 may lie parallel to the transmitting coil antenna to power the tag 104 up if the tag 104 receives enough energy. The energy received may be based a distance of the tag 104 to the transmitting coil antenna and/oe an orientation of the transmitting coil antenna with respect to the tag 104 (e.g., an offset and/or an angle at which the tag 104 faces the transmitting coil antenna, etc.). For example, as the angle between the coil antenna of the tag 104 and the transmitting coil antenna becomes closer to 90 or 270 degrees, antenna energy received by tag 104 may be reduced to zero. As an example, a formula for calculating an amount of energy received by tag 104 from a transmitting coil antenna may be defined according a COSINE (angle). Accordingly, if the angle between the transmitting coil antenna and the coil antenna of the tag 104 reaches 90 or 270 degrees, the energy received by the tag 104 is zero and the tag 104 cannot power up. In this way, if tag 104 is on a syringe 102 and the tag 104 can be placed anywhere on the syringe 102 by a user, there is a possibility that the angle may be close enough to or at the 0 energy point where data encoded in the tag 104 cannot be read by a short range wireless communication device.

Non-limiting embodiments or aspects of flow sensor system 150 including curved coil antenna 600 may reduce and/or eliminate a 90 and/or 270 degree angle between a transmitting coil antenna of the short range wireless communication device of base 180 and tag 104 on syringe 102 by encompassing and/or surrounding syringe 102 with the curved coil antenna 600. For example, and referring to FIG. 8, curved coil antenna 600 may enable magnetic waves to be transmitted out from the short range wireless communication device of base 180 in a radial fashion with respect to syringe 102 when syringe 102 is connected to flow sensor 160 and flow sensor 160 is connected to base 180, thereby covering a larger area of syringe 102 (e.g., depending on a circumferential area of the curved coil antenna 600, an acceptance criteria for successful reads, etc.). As an example, curved coil antenna 600 may enable the magnetic waves to be transmitted radially from the short range wireless communication device of base 180 to encompass an NFC HF RFID tag on a circular syringe. In contrast, a flat NFC coil antenna may result in the magnetic waves being transmitted orthogonal to the coil antenna, which may result in an NFC HF RFID tag that does not line up with the transmitted magnetic waves (e.g., particularly if the tag is 90 degrees to the waves, etc.) not powering up and not transmitting back information encoded on the tag to the transmitting NFC coil antenna. Accordingly, a curved NFC coil antenna may enable magnetic waves to be transmitted in more directions with respect to an NFC HF RFID tag (e.g., for NFC communications based on the NFC standards of ISO14443 and/or ISO15693 which describe physical layer technology and protocol layer technology, etc.), thereby reducing and/or preventing a 90 and/or 270 degree angle between the transmitting coil antenna and the tag.

In some non-limiting embodiments or aspects, fluid injection port 165 of flow sensor 160 may extend from flow tube 162 in a first direction parallel to a longitudinal axis of the fluid injection port 165, and curved coil antenna 600 in the short range wireless communication device of base 180 may be radially curved with respect to the longitudinal axis of the fluid injection port 165 when the flow sensor 160 is connected to the base 180. For example, fluid injection port 165 may be configured to connect to syringe 102 and, when the syringe 102 is connected to the fluid injection port 165 of the flow sensor 160 and the flow sensor 160 is connected to the base 180, curved coil antenna 600 may be radially curved around the syringe 102 and/or extend in the first direction parallel to the longitudinal axis of the fluid injection port 165.

In some non-limiting embodiments or aspects, as shown for example in FIGS. 4A and 6A-6C, curved coil antenna 600 extends in a direction parallel to a plane defined by a face of display 194 of base 180 (e.g., in a direction parallel to a longitudinal axis of syringe 102 when syringe 102 is connected to flow sensor 160 and flow sensor 160 is connected to base 180, etc.). In some non-limiting embodiments or aspects, as shown for example in FIG. 5A, curved coil antenna 600 extends in a direction not parallel (e.g., in a direction perpendicular to) a plane defined by a face of display 194 of base 180 (e.g., in a direction perpendicular to a longitudinal axis of syringe 102 when syringe 102 is connected to flow sensor 160 and flow sensor 160 is connected to base 180, etc.). In such example, curved coil antenna 600 may at least partially surround syringe 102 when syringe 102 is connected to flow sensor 160 and flow sensor 160 is connected to base 180. In some non-limiting embodiments or aspects, a curvature of curved coil antenna may correspond to a circumferential area of a 60 ml syringe, and/or the like.

Referring now to FIGS. 3A-3H and 9A-9E, FIGS. 3A-3H and 9A-9E are flowcharts of non-limiting embodiments or aspects of processes for using a flow sensor system. In some non-limiting embodiments or aspects, one or more of the steps of the processes are performed (e.g., completely, partially, etc.) by flow sensor system 150 (e.g., one or more devices of flow sensor system 150, etc.). In some non-limiting embodiments or aspects, one or more of the steps of the processes are performed (e.g., completely, partially, etc.) by another device or a group of devices separate from or including flow sensor system 150, such as remote computing device 110 (e.g., one or more devices of a system of remote computing device 110, etc.).

Figure 9A:
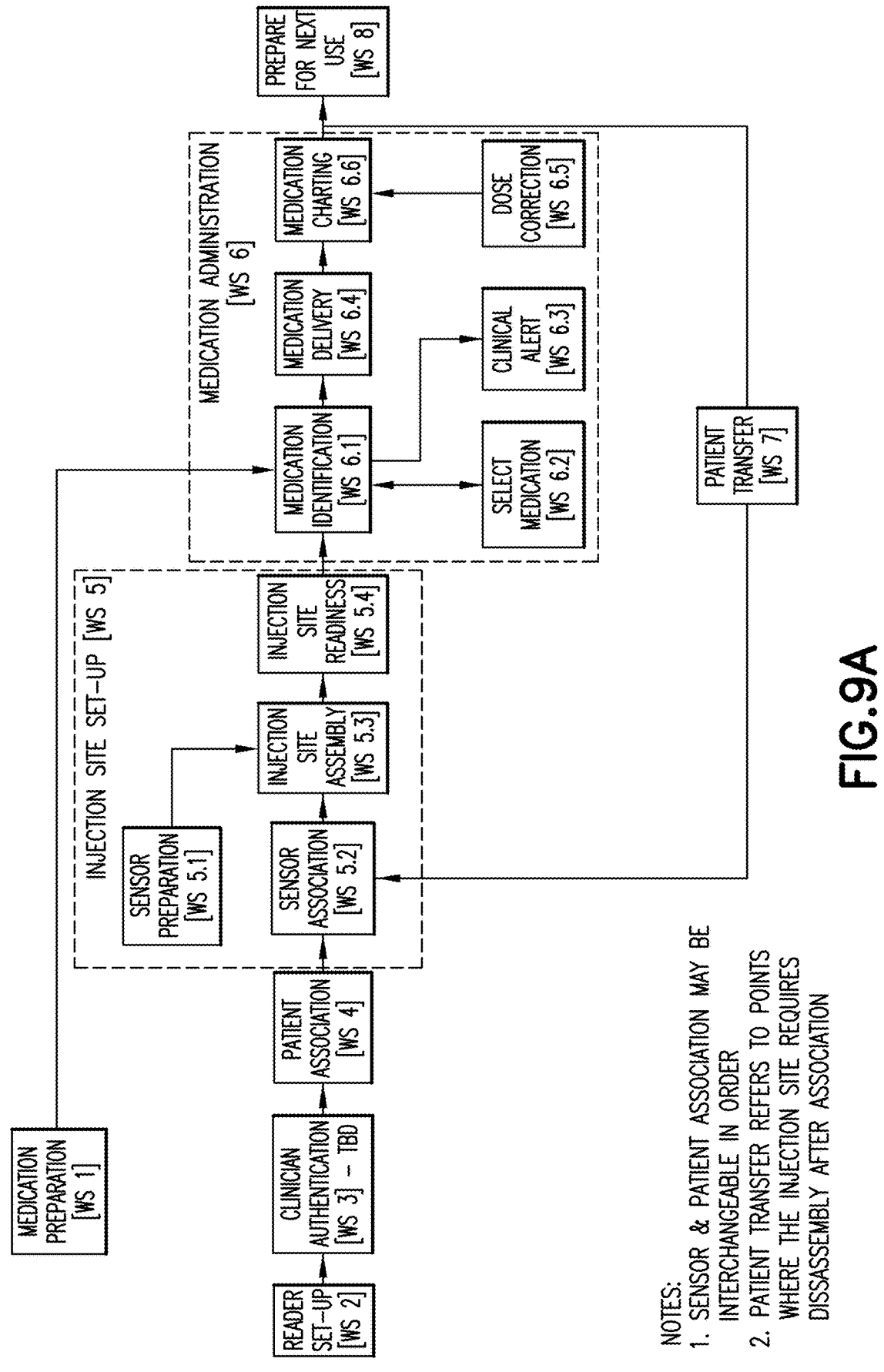
FIG. 9A is a flowchart of non-limiting embodiments or aspects of a process for using a flow sensor system.

As shown in FIG. 9A, at step WS5.2, a process for using a flow sensor system includes scanning a flow sensor label attached to the disposable flow sensor to decode a flow sensor identifier associated with the flow sensor. For example, an optical scanner of base 180 (e.g., "Reader" in FIGS. 9A-9E) for disposable flow sensor 160 (e.g., "Sensor" in FIGS. 9A-9E) may scan a flow sensor label (e.g., a flow sensor barcode, etc.) attached to the disposable flow sensor to decode a flow sensor identifier associated with the flow sensor. As an example, barcode scanning of the disposable flow sensor 160 enables base 180 (and/or remote computing system 110) to determine whether the disposable flow sensor 160 has been used yet or not and, if so, by which patient.

As shown in FIG. 9A, at step WS4, a process for using a flow sensor system includes scanning a patient label attached to a patient to decode a patient identifier associated with the patient. For example, the optical scanner of base 180 for disposable flow sensor 160 may scan a patient label attached to a patient (e.g., a patient wristband, a patient barcode, etc.) to decode a patient identifier associated with the patient. As an example, a smart device (e.g., base 180, etc.) may be utilized to electronically scan, with, for example, a barcode scanner, each of a smart IV consumable (e.g., disposable flow sensor 160, etc.) and the patient wristband provided by an EMR vendor. The smart device may communicate patient identifier information (e.g., Patient MRN) and smart IV consumable unique identification number up to a virtual server (e.g., remote computing device 110, etc.) on a hospital network. The virtual server may utilize patient identifier information to generate a bi-directional link to applications on the Hospital Information System associated to that patient relevant to the function of the smart device and smart consumable. Once the bi-directional link is established, the virtual server may associate the link to the smart IV consumable unique identification number and, if the smart device is disassociated, the smart device, or a new different device, can be re-associated by a scan of the smart consumable. In contrast, if the patient is associated by the electronics alone, such as a patient association to a barcode reader, if that device can no longer be used (e.g., runs out of batteries, etc.) re-association by scanning the patient wristband is required and, if the wristband is not accessible (e.g., during surgery, etc.), manual entry of the patient identifier may need to be performed, which may be be subject to error. For example, a device may need to be associated with a patient record by having the case assigned to the device by the EMR, manually selecting the patient through the user interface on the device or associating the smart device directly to the patient through electronic scan or otherwise. Further, if not properly disassociated, a device may also be at risk of utilization on the incorrect patient recording information to the wrong patient record.

As shown in FIG. 9A, at step WS5.3, a process for using a flow sensor system includes connecting the disposable flow sensor to the base. For example, disposable flow sensor 160 may be connected to base 180.

As shown in FIG. 9A, at step WS5.1, a process for using a flow sensor system includes integrating the disposable flow sensor into an IV line. For example, disposable flow sensor 160 may be integrated into IV line 106.

Figure 9B:
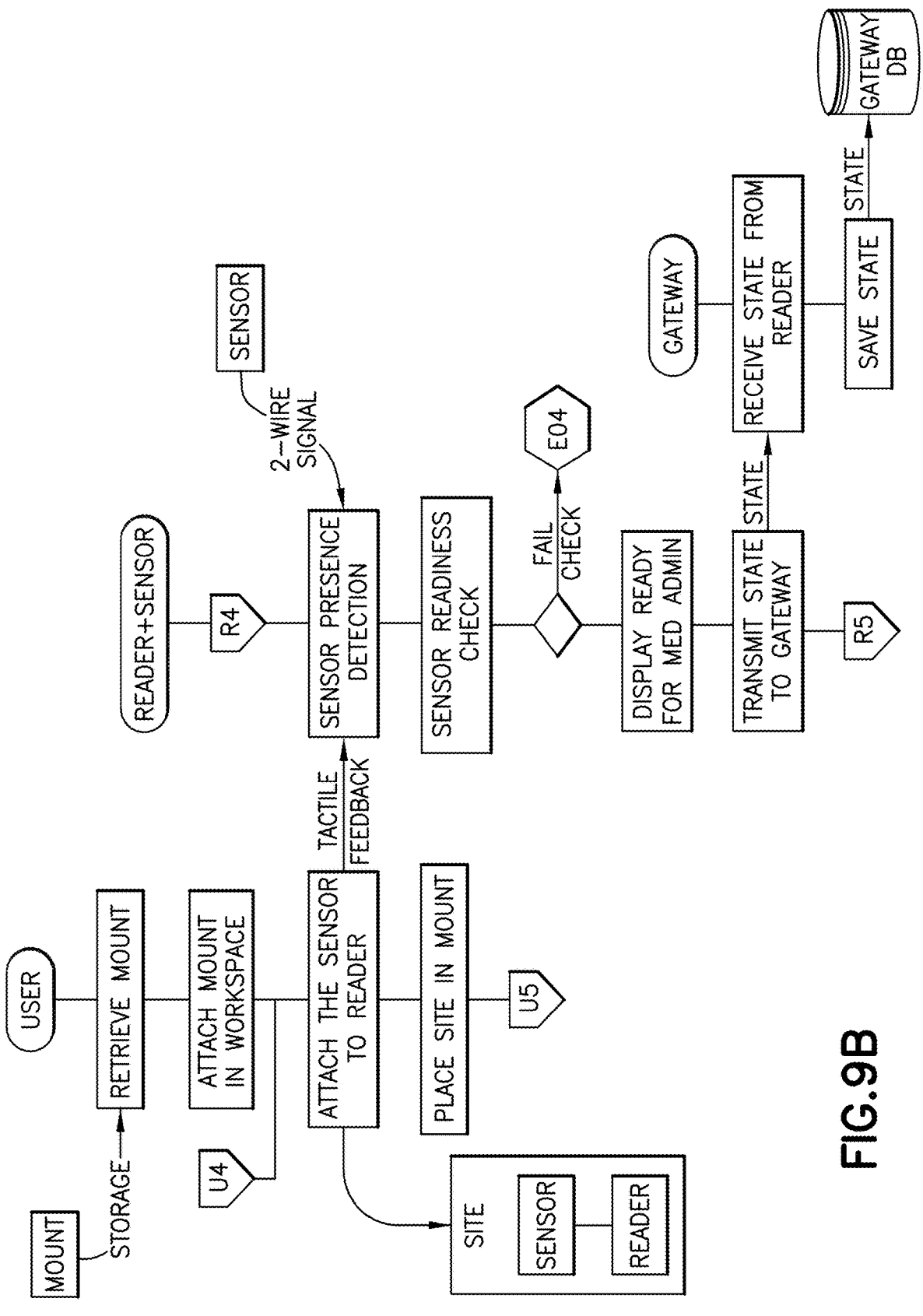
FIG. 9B is a flowchart of non-limiting embodiments or aspects of a process for using a flow sensor system.

In some non-limiting embodiments or aspects, and referring now to FIG. 9B, disposable flow sensor 160 is integrated into IV line 106 before scanning the flow sensor label, scanning the patient label, and connecting the disposable flow sensor 160 to the base 180. For example, integrating disposable flow sensor 160 into IV line 106 before scanning the flow sensor label, scanning the patient label, and connecting the disposable flow sensor 160 to the base 180 may enable a clinician to associate the patient when performing other positive patient identification and/or to scan and attach the disposable flow sensor 160 in one more contiguous step which adds value, for example, when setting up a patient for a procedure in an operating room. As an example, scanning the patient ID prior to connecting may ensure that the IV line 106 does not hinder a user in scanning the patient ID, which may be ideal for outpatients where a new IV line is built with the disposable flow sensor 160 in place for the procedure.

Figure 9C:
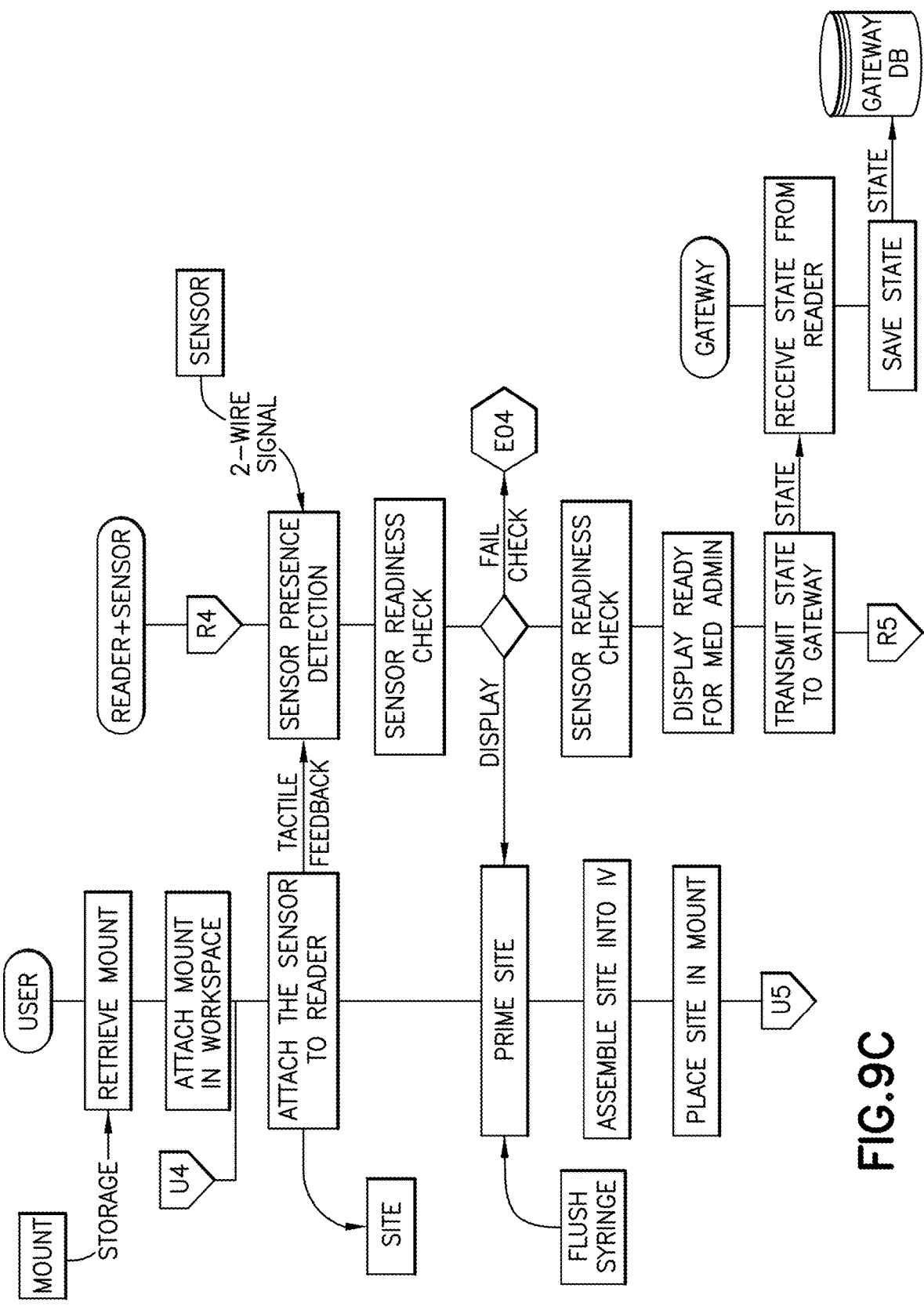
FIG. 9C is a flowchart of non-limiting embodiments or aspects of a process for using a flow sensor system.

In some non-limiting embodiments or aspects, and referring now to FIG. 9C, disposable flow sensor 160 is integrated into IV line 106 after scanning the flow sensor label, scanning the patient label, and connecting the disposable flow sensor 160 to the base 180. For example, integrating disposable flow sensor 160 into IV line 106 after scanning the flow sensor label, scanning the patient label, and connecting the disposable flow sensor 160 to the base 180 may enable a clinician to prepare the base 180 and disposable flow sensor 160 prior to interaction with a patient and/or a pre-existing IV, which may add value when the clinician has time prior to the arrival of an inpatient with a pre-existing IV saving steps that need not be performed in the presence of the patient.

As shown in FIG. 9A, at steps WS4, WS5.2, and/or WS5.4, a process for using a flow sensor system includes communicating the flow sensor identifier and the patient identifier to a remote computing device and associating the flow sensor identifier with the patient identifier. For example, base 180 may communicate the flow sensor identifier and the patient identifier to remote computing device 110, and remote computing device 110 may associate the flow sensor identifier with the patient identifier in a database.

Figure 9D:
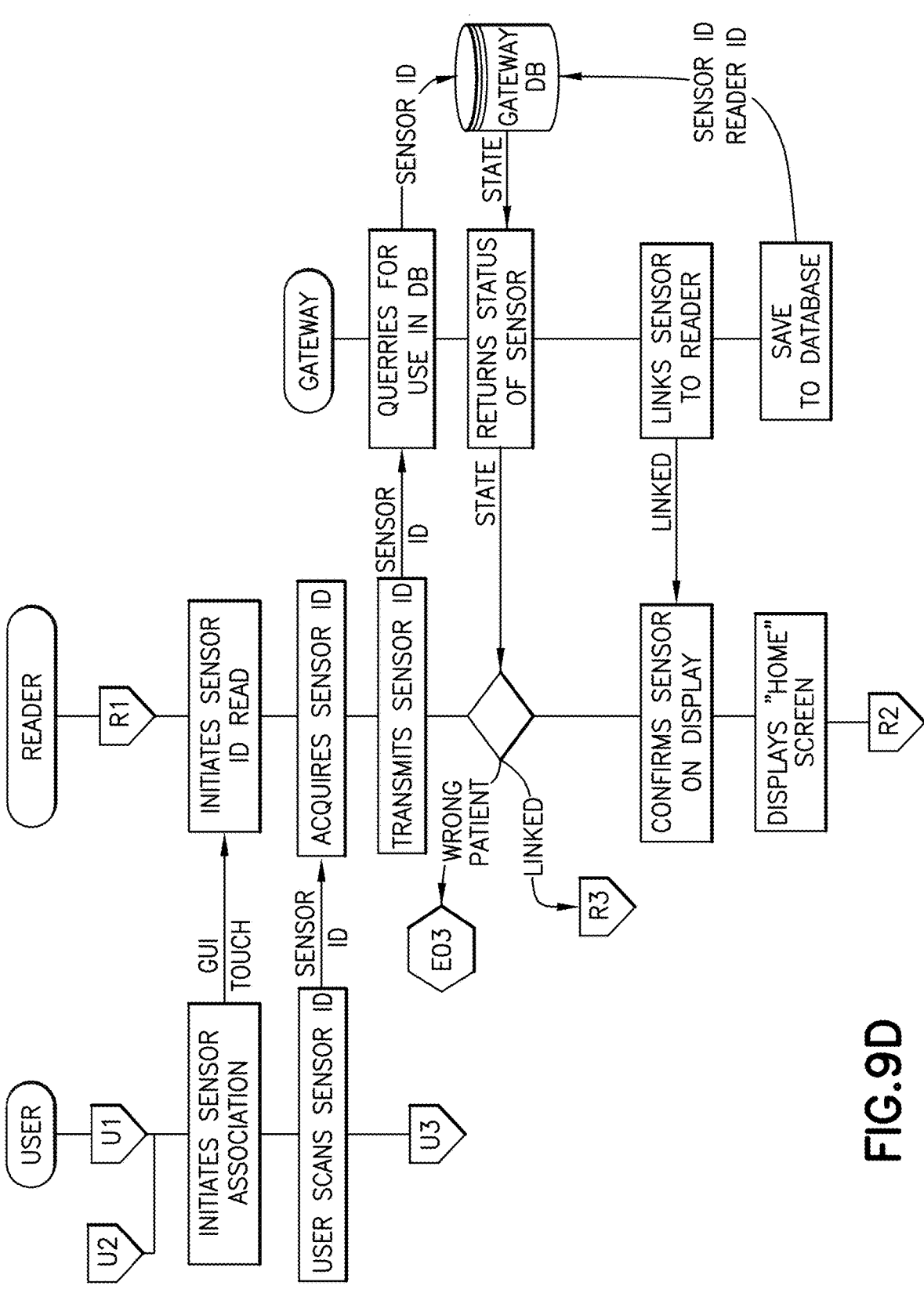
FIG. 9D is a flowchart of non-limiting embodiments or aspects of a process for using a flow sensor system.

In some non-limiting embodiments or aspects, and referring now to FIG. 9D, base 180 may communicate, to remote computing device 110, a request for a status of the disposable flow sensor 160 associated with the flow sensor identifier and receive, from remote computing device 110, an indication of the status of the disposable flow sensor 160 associated with the flow sensor identifier. For example, the indication of the status of the disposable flow sensor 160 may include an indication of whether the flow sensor identifier of the disposable flow sensor 160 is associated with the patient identifier of the patient.

In some non-limiting embodiments or aspects, and still referring to FIG. 9D, base 180 may communicate, to remote computing device 110, a base identifier associated with the base 180 in the request for the status of the disposable flow sensor 160 associated with the flow sensor identifier, and remote computing device 110 may associate the base identifier with the flow sensor identifier and the patient identifier.

As shown in FIG. 9A, at steps WS4 and/or WS6, a process for using a flow sensor system includes communicating a request for information associated with the patient associated with the patient identifier, receiving the information associated with the patient, and displaying the information associated with the patient. For example, and referring also to FIG. 9E, base 180 may communicate, to remote computing device 110, a request for information associated with the patient associated with the patient identifier, receive, from remote computing device 110, the information associated with the patient, and display, with a display, the information associated with the patient.

In some non-limiting embodiments or aspects, the information associated with the patient includes at least one of a list of medication allergies associated with the patient and a list of medication doses pending for the patient.

In some non-limiting embodiments or aspects, and still referring to FIG. 9E, a short range wireless communication device of base 180 may scan a short range wireless communication tag 104 attached to a syringe 102 to decode a medication identifier associated with a medication in the syringe 102, and the base 180 may compare the medication identifier to the at least one of the list of medication allergies associated with the patient and the list of medication doses pending for the patient. For example, a display 194 of the base 180 may display an alert associated with administration of the medication to the patient based on the comparison. In some non-limiting embodiments or aspects, the short range wireless communication device includes a near-field communication (NFC) receiver, and wherein the short range wireless communication tag includes a NFC tag.

Accordingly, non-limiting embodiments or aspects of a process for using a flow sensor system may enable more steps to be performed at ae site of care with a patient in view which provides advantages over methods that require interaction with EMR screens. Further, non-limiting embodiments or aspects of a process for using a flow sensor system may enable a patient to be associated with the smart consumable that is attached to the patient IV line rather than the electronics (e.g., base 180, etc.) alone, which provides for higher confidence that the device data is linked to the proper patient as the smart IV consumable is directly attached to the patient (through the IV), and which may enable the smart device to be swapped with another that can be associated to the patient by a scan of the smart consumable as opposed to being required to re-scan the patient wristband.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system comprising:
a flow sensor including:
   a flow tube including a fluid inlet at a first end of the flow tube, a fluid outlet at a second end of the flow tube opposite the first end of the flow tube, a fluid injection port between the first end and the second end of the flow tube, wherein the fluid injection port extends from the flow tube in a first direction parallel to a longitudinal axis of the fluid injection port; and
a base configured to connect to the flow sensor, wherein the base includes:
   a short range wireless communication device including a curved coil antenna, wherein the curved coil antenna is radially curved with respect to the longitudinal axis of the fluid injection port when the flow sensor is connected to the base, and wherein the curved coil antenna has a partial cylinder shape; and
   a display, wherein the curved coil antenna extends in a direction perpendicular to a plane defined by a face of the display.

2. The system of claim 1, wherein the curved coil antenna extends in the first direction parallel to the longitudinal axis of the fluid injection port.

3. The system of claim 1, wherein the base further includes the display, and wherein the curved coil antenna extends in a direction parallel to a plane defined by the face of the display.

4. The system of claim 1, wherein the fluid injection port is configured to connect to a syringe, and wherein, when the syringe is connected to the fluid injection port of the flow sensor and the flow sensor is connected to the base, the curved coil antenna is radially curved around the syringe.

5. The system of claim 4, wherein a short range wireless communication tag attached is attached to a body of the syringe.

6. The system of claim 5, wherein the short range wireless communication device is configured to automatically communicate with the short range wireless communication tag on the syringe via a short range wireless communication connection when the short range wireless communication tag is brought within a communication range of the short range wireless communication device.

7. The system of claim 6, wherein the short range wireless communication device receives information associated with a medication included in the syringe from the short range wireless communication tag when the short range wireless communication tag is brought within the communication range of the short range wireless communication device.

8. The system of claim 1, wherein the short range wireless communication device includes a near-field communication (NFC) receiver.

9. A system comprising:
a flow sensor including:
   a flow tube including a fluid inlet at a first end of the flow tube, a fluid outlet at a second end of the flow tube opposite the first end of the flow tube, a fluid injection port between the first end and the second end of the flow tube, wherein the fluid injection port is configured to connect to a syringe; and
a base configured to connect to the flow sensor, wherein the base includes:
   a short range wireless communication device including a curved coil antenna, wherein, when the syringe is connected to the fluid injection port of the flow sensor and the flow sensor is connected to the base, the curved coil antenna is radially curved around the syringe, and wherein the curved coil antenna has a partial cylinder shape; and
   a display, wherein the curved coil antenna extends in a direction perpendicular to a plane defined by a face of the display.

10. The system of claim 9, wherein the curved coil antenna extends in a first direction parallel to a longitudinal axis of the syringe when the syringe is connected to the fluid injection port of the flow sensor and the flow sensor is connected to the base.

11. The system of claim 9, wherein the base further includes the display, and wherein the curved coil antenna extends in a direction parallel to a plane defined by the face of the display.

12. The system of claim 9, wherein a short range wireless communication tag attached is attached to a body of the syringe.

13. The system of claim 12, wherein the short range wireless communication device is configured to automatically communicate with the short range wireless communication tag on the syringe via a short range wireless communication connection when the short range wireless communication tag is brought within a communication range of the short range wireless communication device.

14. The system of claim 13, wherein the short range wireless communication device receives information associated with a medication included in the syringe from the short range wireless communication tag when the short range wireless communication tag is brought within the
communication range of the short range wireless commu-
nication device.

15. The system of claim 9, wherein the short range
wireless communication device includes a near-field com-
munication (NFC) receiver.

16. A base for a flow sensor, comprising:
a housing including:
an opening configured to receive the flow sensor;
one or more processors;
a display; and
a short range wireless communication device including
a curved coil antenna, wherein the curved coil
antenna has a partial cylinder shape, and wherein the
curved coil antenna extends in a direction perpen-
dicular to a plane defined by a face of the display.

17. The base of claim 16, wherein the curved coil antenna
extends in a direction parallel to a plane defined by the face
of the display.

18. The base of claim 16, wherein the curved coil antenna
is radially curved around a syringe when the syringe is
connected to the flow sensor and the flow sensor is con-
nected to the base.

19. The base of claim 18, wherein a short range wireless
communication tag attached is attached to a body of the
syringe.

20. The base of claim 19, wherein the short range wireless
communication device is configured to automatically com-
municate with the short range wireless communication tag
on the syringe via a short range wireless communication
connection when the short range wireless communication
tag is brought within a communication range of the short
range wireless communication device.

21. The base of claim 20, wherein the short range wireless
communication device receives information associated with
a medication included in the syringe from the short range
wireless communication tag when the short range wireless
communication tag is brought within the communication
range of the short range wireless communication device.

22. The base of claim 16, wherein the short range wireless
communication device includes a near-field communication
(NFC) receiver.

*     *     *     *     *